United States Patent
Wang et al.

(10) Patent No.: US 11,948,345 B2
(45) Date of Patent: Apr. 2, 2024

(54) ULTRASOUND SYSTEM WITH ARTIFICIAL NEURAL NETWORK FOR RETRIEVAL OF IMAGING PARAMETER SETTINGS FOR RECURRING PATIENT

(71) Applicant: KONINKLIJKE PHILIPS N.V., Eindhoven (NL)

(72) Inventors: Haibo Wang, Melrose, MA (US); Hua Xie, Cambridge, MA (US); Grzegorz Andrzej Toporek, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 95 days.

(21) Appl. No.: 17/046,387

(22) PCT Filed: Apr. 9, 2019

(86) PCT No.: PCT/EP2019/058998
§ 371 (c)(1),
(2) Date: Oct. 9, 2020

(87) PCT Pub. No.: WO2019/197427
PCT Pub. Date: Oct. 17, 2019

(65) Prior Publication Data
US 2021/0093301 A1    Apr. 1, 2021

Related U.S. Application Data

(60) Provisional application No. 62/654,863, filed on Apr. 9, 2018.

(51) Int. Cl.
*G06V 10/764*    (2022.01)
*A61B 8/00*    (2006.01)
(Continued)

(52) U.S. Cl.
CPC ............ *G06V 10/764* (2022.01); *A61B 8/463* (2013.01); *A61B 8/467* (2013.01); *A61B 8/5207* (2013.01);
(Continued)

(58) Field of Classification Search
CPC ........... A61B 8/54; A61B 8/463; A61B 8/467; A61B 8/5207; A61B 8/5223; G06B 40/16; G06B 2201/03; G06K 9/6271
See application file for complete search history.

(56) References Cited

U.S. PATENT DOCUMENTS 6,530,885 B1    3/2003   Entrekin et al.
6,979,294 B1   12/2005   Selzer et al.
(Continued)

FOREIGN PATENT DOCUMENTS

CN    107480701 A        12/2017
WO    WO-0224049 A2  *   3/2002   ............. A61B 34/20

OTHER PUBLICATIONS

Mohammed et al: "Neural Network and Multi-Fractal Dimension Features for Breast Cancer Classification From Ultrasound Images"; Computers and Electrical Engineering, 2013, pp. 872-882.
(Continued)

*Primary Examiner* — Katherine L Fernandez
*Assistant Examiner* — Brooke Lyn Klein

(57) ABSTRACT

A system and method for ultrasound imaging may involve the use of an ultrasound probe and a processor coupled to the probe and to a source of previously-acquired ultrasound image data. The processor may be configured to receive patient identification information (e.g., responsive to user input and/or supplemented by additional information such a photo of the patient), to determine whether the patient identification information identifies a recurring patient, and if so, to retrieve, from the source of previously-acquired
(Continued)

ultrasound image data, previous ultrasound images associated with the recurring patient. The processor may be further configured to generate a current ultrasound image based on signals received from the prove and to apply a neural network to the current ultrasound image and the previous ultrasound images to identify a matching pair of images, such that imaging settings from the matched previous image may be applied to the system for subsequent imaging.

22 Claims, 10 Drawing Sheets

(51) Int. Cl.
    *A61B 8/08*           (2006.01)
    *G06F 18/2413*    (2023.01)
    *G06V 10/82*      (2022.01)
    *G06V 40/16*      (2022.01)

(52) U.S. Cl.
    CPC .............. *A61B 8/5223* (2013.01); *A61B 8/54* (2013.01); *G06F 18/24133* (2023.01); *G06V 10/82* (2022.01); *G06V 40/16* (2022.01); *G06V 2201/03* (2022.01)

(56) References Cited

U.S. PATENT DOCUMENTS

| | | |
|---|---|---|
| 7,074,187 B2 | 7/2006 | Selzer et al. |
| 2004/0077952 A1 | 4/2004 | Rafter et al. |
| 2004/0147840 A1* | 7/2004 | Duggirala ............. G06T 7/0012 |
| | | 600/437 |
| 2006/0036522 A1* | 2/2006 | Perham ................. G06Q 40/06 |
| | | 705/35 |
| 2012/0108960 A1* | 5/2012 | Halmann ............. A61B 8/5292 |
| | | 715/810 |
| 2013/0131512 A1 | 5/2013 | Kim |
| 2013/0253317 A1 | 9/2013 | Gauthier |
| 2015/0272546 A1* | 10/2015 | Cheon ................... G06T 7/0012 |
| | | 600/440 |
| 2016/0217260 A1* | 7/2016 | Aarts ..................... G16H 40/20 |
| 2016/0317127 A1* | 11/2016 | dos Santos Mendonca ............... |
| | | G16Z 99/00 |
| 2017/0262598 A1* | 9/2017 | Petkov ................... G06T 15/06 |
| 2017/0360403 A1 | 12/2017 | Rothberg et al. |
| 2018/0075597 A1* | 3/2018 | Zhou ..................... A61B 6/037 |
| 2018/0114056 A1* | 4/2018 | Wang ................. G06V 10/7715 |
| 2018/0137244 A1* | 5/2018 | Sorenson ............... G16H 30/20 |
| 2018/0144243 A1* | 5/2018 | Hsieh ..................... G06F 11/30 |
| 2018/0161015 A1* | 6/2018 | Hollaender .......... G01S 7/52049 |
| 2018/0322629 A1* | 11/2018 | Hu ......................... G06N 3/084 |
| 2018/0342060 A1* | 11/2018 | Yao ....................... G16H 40/63 |
| 2019/0008480 A1* | 1/2019 | Gerard ................. A61B 8/5246 |
| 2019/0183453 A1* | 6/2019 | Schwab ............... A61B 8/5246 |
| 2020/0160521 A1* | 5/2020 | Wang ................... G06V 40/197 |
| 2021/0279874 A1* | 9/2021 | Boyd ................... A61B 5/0013 |

OTHER PUBLICATIONS

PCT/EP2019/058998 ISR 7 WO, Jul. 5, 2019, 15 Pages.

* cited by examiner

ULTRASOUND SYSTEM WITH ARTIFICIAL NEURAL NETWORK FOR RETRIEVAL OF IMAGING PARAMETER SETTINGS FOR RECURRING PATIENT

CROSS-REFERENCE TO PRIOR APPLICATIONS

This application is the U.S. National Phase application under 35 U.S.C. § 371 of International Application No. PCT/EP2019/058998, filed on Apr. 9, 2019, which claims the benefit U.S. Provisional Patent Application No. 62/654,863, filed on Apr. 9, 2018. These applications are hereby incorporated by reference herein.

TECHNICAL FIELD

The present disclosure pertains to ultrasound imaging systems and methods and particularly to systems and methods for subsequent imaging of recurring patients and the retrieval of image acquisition settings using an artificial neural network.

BACKGROUND

Ultrasound imaging is commonly used to non-invasively image internal tissue or organs of a patient, e.g., for diagnosing any number of different diseases and the progression or success of treatment thereof. In order to suitably adapt the image acquisition for a specific patient, organ, or a specific disease, numerous imaging parameters of the imaging system may need to be set appropriately. These parameters are related to the transmission and reception of the ultrasound signals, the processing of the acquired signals, image reconstruction, image display, and image storage. They include such operating parameters as the depth of an image, the location of the transmit focus, the number of focal zones, whether to use the B mode or color Doppler mode, whether harmonic or fundamental frequencies are to be used for imaging, image resolution, frame rate etc. For example, in the context of monitoring cancer treatment, the same ultrasound scanner may be used for multiple patients and the settings may be changed between patients.

Manually changing the parameters for every acquisition is time consuming and error-prone. Therefore, many systems include tissue-specific presets (TSP), which are a set of imaging parameter values that have been optimized for a particular application, for example imaging of the liver or imaging of the carotid artery. With any given ultrasound transducer, the manufacturer typically offers a selection of tissue-specific presets that the user may choose from to quickly set up the ultrasound scanner for a particular imaging task. Often, these general presets need to be changed and further adapted to specific patients. Existing systems that provide some level of automation of the setting of patient-specific settings may not provide a sufficiently robust solution and alternative and/or improved methods for automatically retrieving patient-specific imaging parameter settings may be desirable.

SUMMARY

The present disclosure describes ultrasound imaging systems equipped with an artificial neural network trained for the automated retrieval of imaging parameter settings for recurring patients.

An ultrasound imaging system in accordance with some embodiments may include ultrasound probe and a processor communicatively coupled to the ultrasound probe and to a source of previously-acquired ultrasound image data. The source of previously-acquired ultrasound image data may include a storage device (e.g., one or more hard disk drives, solid state drives, or any other type of suitable storage device comprising non-volatile memory). The processor of the system may include one or more processing units (e.g., one or more single or multi-core CPUs, a single GPU or GPU cluster, or any arrangement of multiple processors configured for example for parallel processing) and uniquely configured to perform the functions described herein. In some embodiments, the processor may be configured to receive patient identification information (e.g., responsive to user input and/or supplemented by additional information such a photo of the patient), to determine whether the patient identification information identifies a recurring patient, and if the patient identification information identifies a recurring patient, to retrieve, from the source of previously-acquired ultrasound image data, previous ultrasound images associated with the recurring patient. The processor is also configured to generate a current ultrasound image and to apply a neural network to the current ultrasound image and the previous ultrasound images to identify a matching pair of images. For example, the processor may provide, for each of a plurality of the previous ultrasound images, a pair of ultrasound images that includes the current ultrasound image and one of the plurality of previous ultrasound images to the neural network, which may be trained to determine whether the pair of images represent the same imaging plane through the biological tissue of the recurring patient. If a determination is made by the neural network that the pair of images corresponds to a matching pair, the processor is configured to automatically adjust one or more imaging parameters of the ultrasound imaging system such that they correspond to imaging parameter settings associated with the previously-acquired image in the pair and to generate a new ultrasound image using the adjusted imaging parameters.

In some embodiments, the neural network may include at least one neural network, which may be configured to covert the input images, and in some cases in combination with the corresponding imaging settings, to respective feature vectors. For example, the neural network may be a deep neural network including a pair of branches, each comprising a neural network (e.g., a convolutional neural network) and operating in parallel to process each of the images in the pair and output a feature factor describing each of the images in the pair. The feature vectors may then be compared (e.g., by computing a distance metric) to determine a similarity or match between the two images. Additional examples of systems are described further below, the components of which may be used in any suitable combination with one another in addition to the specific combinations described.

A method in accordance with some examples herein may involve the steps of receiving patient identification information, determining whether the patient identification information identifies a recurring patient, and upon determination that the patient identification information identifies a recurring patient, automatically retrieving a plurality of previous ultrasound images associated with the recurring patient from a source of previously-acquired ultrasound image data. The method may further involve generating a current ultrasound image of biological tissue of the recurring patient, providing the current ultrasound image and the plurality of previous ultrasound images to a neural network to identify a previous matching image, and responsive to an identification of the matching previous image, automatically adjusting one or more imaging parameters of the ultrasound imaging system to correspond to imaging parameter settings associated with matching previous image and acquiring a new ultrasound image with the adjusted imaging parameters. In some examples, the determination of a previous matching image may be made upon an identification of a previously acquired image of the recurring patient that represents the biological tissue at the same imaging plane as the imaging plane of the currently acquired ultrasound image. In some embodiments, the method may further involve the concurrent display of the two images being matched (e.g., the current ultrasound image and a dynamically updating display that cycles through each of the previously acquired images as the comparison of the previous image with the current image is being performed). Additional examples of methods are described further below, the process blocks or steps of which may be performed in any suitable order or combination with one another in addition to the specific examples described.

Any of the methods described herein, or steps thereof, may be embodied in non-transitory computer-readable medium comprising executable instructions, which when executed by a processor (e.g., of a medical imaging system) may cause the processor to perform the method or steps embodied therein.

DETAILED DESCRIPTION

The following description of certain embodiments is merely exemplary in nature and is in no way intended to limit the invention or its applications or uses. In the following detailed description of embodiments of the present systems and methods, reference is made to the accompanying drawings which form a part hereof, and which are shown by way of illustration specific embodiments in which the described systems and methods may be practiced. These embodiments are described in sufficient detail to enable those skilled in the art to practice presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

Figure 7B:
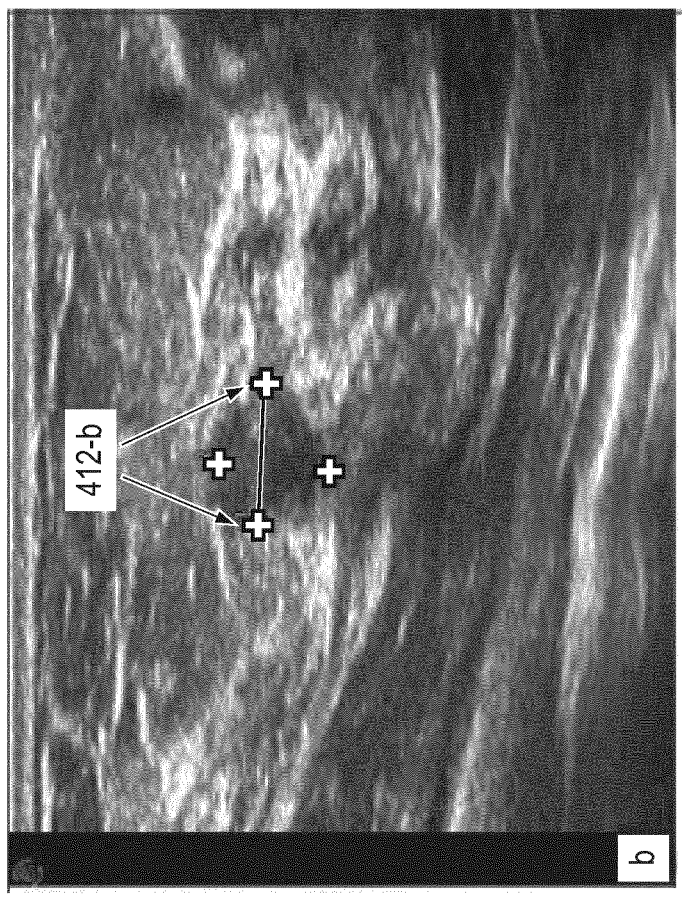
FIGS. 7A and 7B show ultrasound images of the same breast lesion acquired with different imaging parameter settings.
Figure 7A:
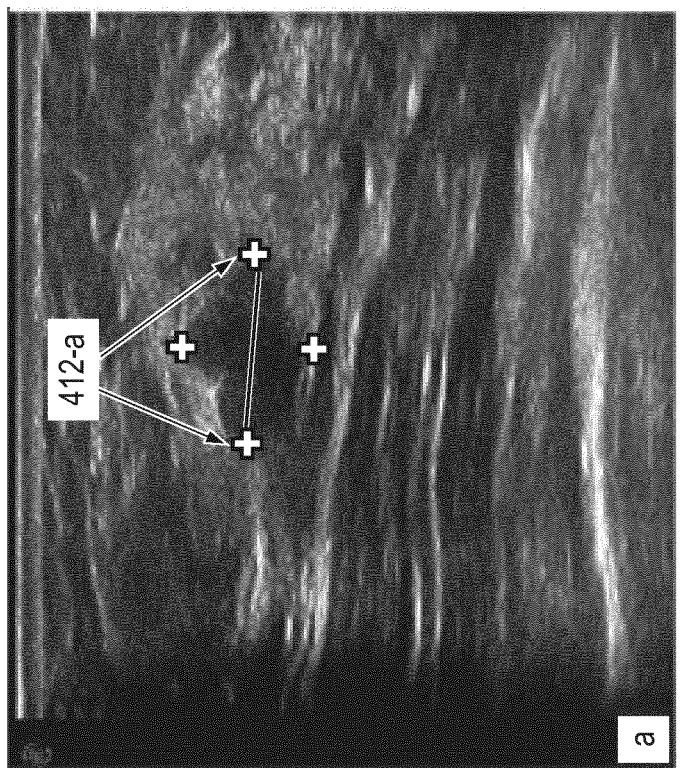
Figure 8B:
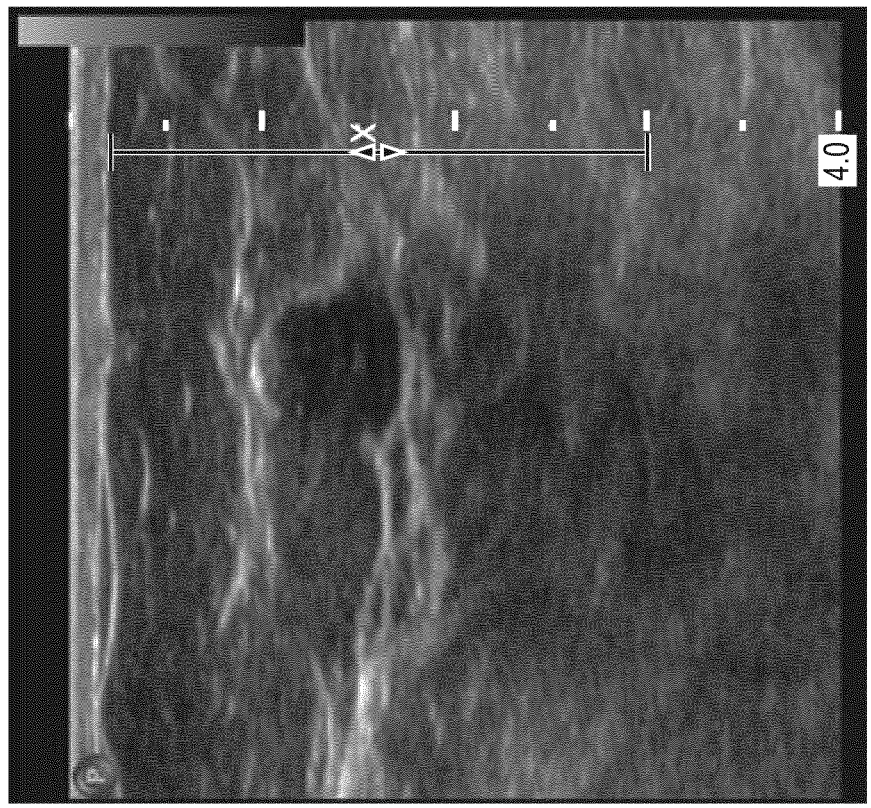
FIGS. 8A and 8B show ultrasound images of the same breast lesion acquired at two different points in time with the same acquisition settings.
Figure 8A:
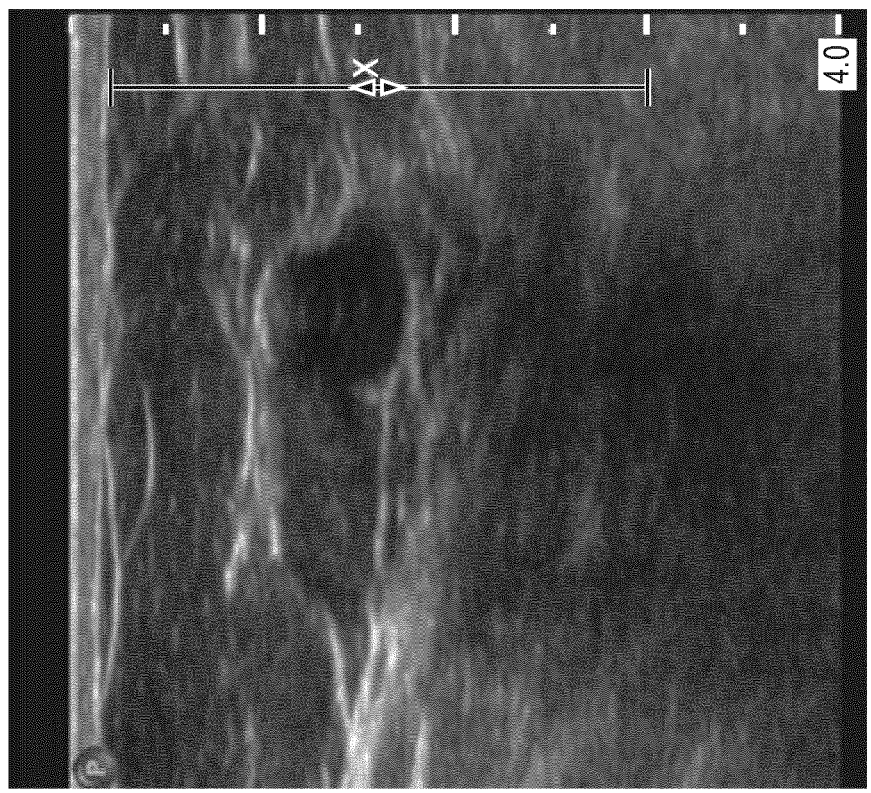

For a patient needing follow-up ultrasound examinations, the same imaging parameter settings (also referred to as acquisition parameter settings, or simply imaging settings or acquisition settings), which may include system acquisition states and patient specific adjustments, should be applied for measurement consistency. However, in clinical practice, it is likely that multiple operators would be involved in the serial exams of the same patient, and therefore the imaging settings can vary, in some cases significantly, from a previous exam to a current one. For example, the same region of interest (e.g., a breast lesion of the same patient) may appear very differently on an image acquired using different acquisition settings, e.g., as shown in FIGS. 7A and 7B, the latter being of an image acquired using higher transmit power to produce the image. Measurement accuracy (e.g., as indicated by the measurement markers 412-*a* and 412-*b* in FIGS. 7A and 7B, respectively, which may suggest shrinking of the suspicious region) and subsequent diagnosis may be adversely affected by this variation. In contrast, the variation in images of an ROI (e.g., of a breast lesion, as shown in FIGS. 8A and 8B), even if acquired during temporally spaced exams, may be greatly reduced by applying the same acquisition settings. To reduce operator variability and thus the risk of diagnostic inaccuracy and to simplify the imaging workflow, a system and method for automatically retrieving image acquisition settings in longitudinal studies is described herein. In some embodiments herein, the system and methods may be fully automated in terms of patient identification, setting retrieval, appropriate view acquisition, and image archiving. In examples described herein, the system is operable to apply imaging settings that are specific not only to a particular patient but also to a particular imaging application (e.g., specific to the tissue or organ being imaged and/or a particular view of the tissue or organ being imaged).

Figure 1:
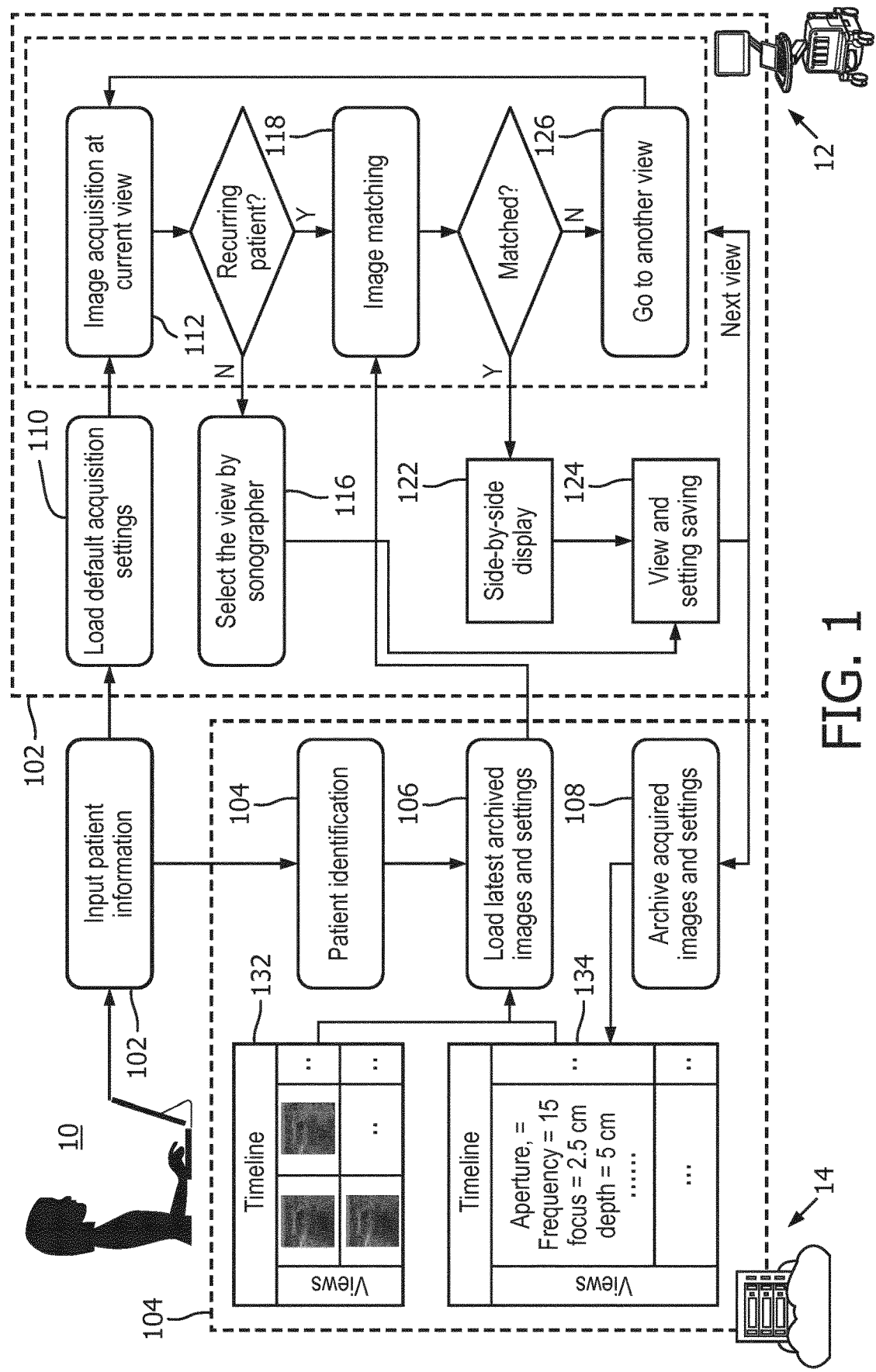
FIG. 1 is a flow diagram of an ultrasound imaging process in accordance with the principles of the present disclosure.

With reference now to FIG. 1, an operational scenario for ultrasonically inspecting biological tissue of a patient is described to facilitate understanding of aspects of the present invention. As shown in block 102 of FIG. 1, initially, a sonographer may input patient identification information via a user interface device (e.g., a control panel, keyboard, touch screen, or the like) of an ultrasound scanner 12. The scanner 12 may be part of a networked system 10, which may include one or more processing units co-located with the scanner 12 (e.g., part of the ultrasound scanner itself) or remotely located (e.g., on a remote computing device 14 such as a cloud server). The patient identification information may include any combination of personal identifying information that may be used to identify the patient, such as the patient's first and/or last name, patient's ID number or any other type of unique medical record identifier, patient's date of birth, etc. The patient identification information may be input at or before the start of an ultrasound exam and may be used by the scanner 12, the remote computing device 14, or a combination thereof, to determine whether the patient is a recurring patient.

To make a recurring patient determination, the system 10 accesses stored patient identification information, which may be stored in a patient database. As illustrated, the recurring patient determination (e.g., at block 104) may be made remotely (e.g., by the remote computing device 14, as shown in block 104), or locally on the ultrasound imaging system (e.g., as part of processing block 102). During the recurring patient determination, the newly input patient identification information may be matched to the stored patient identification information to determine whether the newly input patient identification information matches (precisely or approximately), any of the patient records within the patient database and thus make a determination on whether the patient is a recurring patient. In some embodiments, a rules-based decision tree (e.g., a sequence of if-then constructs) may be used by a processing unit of either the scanner 12 or the remote computing device 14 to perform the patient identification information matching. A rules-based decision tree may be used, for example, to approximately or precisely match one or more input fields or certain percentage of the input fields (e.g., 80%, 90% of the input fields, in some cases assigning higher priority to certain input fields such as the unique medical record identifier and/or the patient's last name during the matching process). In some embodiments, a properly trained artificial neural network may be used to perform or assist the recurring patient determination.

For example, when the recurring patient determination is performed by the remote computing device 14 (e.g., using a rules-based approach or a by applying a properly trained machine learning model), the patient identification information received by the scanner 12 may be transmitted, as shown in block 104, to the remote computing device 14, which then accesses the stored patient identification information to perform the matching. In some examples, the scanner 12 may additionally or alternatively perform the patient matching (e.g., using a rules-based approach or a by applying a properly trained machine learning model). In such examples, the scanner 12 may, upon entry of new patient identification information, transmit a request to the remote computing device 14 to retrieve the stored patient identification information and perform the patient matching locally.

If a matching patient record is identified in the patient database, a determination is made by the system 10 that the patient is a recurring patent, and the processed proceeds to block 118. Alternatively, if a determination is made that the patient is not a recurring patient, the process continues to block 116, where imaging continues with the default acquisition settings (or as may be further manually adjusted by the sonographer). Ultrasound images acquired under this scenario along with the corresponding imaging settings are stored locally initially, as shown in block 124, and then archived, as shown in block 108. As described, in some embodiments, the identification of whether the patient is either recurring or not, may be performed by the ultrasound scanner 12 and/or in combination with the remote computing device 14. For example, the remote computing device 14, which may include a cloud server, may comprise a data storage device that stores the patient database, while a processor of the scanner 12 may perform the actual determination of whether the patient is a recurring patient, e.g., based on executable instructions (e.g., source code or compiled code) stored on the scanner. The executable instructions may implement a set of predetermined rules (i.e. decision logic) or they may, additionally or alternatively, implement a properly trained machine-learning model. In some embodiments, the determination of whether the patient is a recurring patient may instead be performed by the remote computing device 14 and the determination decision may be supplied to the scanner 12 (e.g., for displaying a notification to the sonographer) and/or used by the remote computing device 14 for the retrieval of prior image data associated with the recurring patient.

In some cases, the patient identification information may be noisy (e.g., the information may be partial and/or include typographical errors in one or more of the data entries noted above). The system 10 may employ a properly trained machine learning model (also referred to as patient matching model) to resolve errors or noise in the patient identification input data. In some examples, additional patient identification information, for example a patient image may be provided to the system 100 in addition to any text input that may be provided by the sonographer. The patient image may be automatically captured, e.g., at the start of the exam, by an image capture device (e.g., a digital camera) appropriately positioned to include the patient's face within its field of view. In other examples, the patient image may be captured before the start of the exam, for example at the time of patient check in with the medical facility. The patient image may be communicated (via a wired or wireless connection) from the image capture device or a storage device to the relevant processing unit of system 10 that performs the recurring patient determination. The system may employ any currently known or later developed face recognition techniques to match the patient's face in the patient image to that in a previous patient image (e.g., from a prior exam). In some examples, alternatively or additionally, the system 10 may be configured to receive confirmatory user input to complete the recurring patient determination process. For example, the system 10 may identify a small group of patients (e.g., three or more) from the larger list of unique patient records in the patient database that are determined to be most likely matches to the current patient. The system 10 may display a list of the patients in the small group to the user and await confirmatory input (e.g., a selection of one of the patients in the list or none) before proceeding to the next steps (e.g., assisted exam through view matching or unassisted exam). In some such embodiments, when displaying the list of most likely matching patients, the system 10 may highlight any or part of the non-matching information to increase the operator's awareness of discrepancies and potentially facilitate an easier decision-making by the operator.

As described, in yet further embodiments, the system 10 may additionally or alternatively employ a neural network for the determination of whether the patient is a recurring patient. The neural network may receive, as input, the patient identification information, which may include identifying information such as name, medical records identifier, date of birth, etc. and/or one or more patient images. The neural network may be trained to perform face recognition (in the case when patient images are included in the patient identification information) and/or compute a probability of a match between the input data and individual records of the stored patient identification data. The neural network may output the probabilities of a match and/or, in some examples, a determination that the patient is a recurring patient may be automatically made when the probability exceeds a certain value (e.g., 80%, 85%, 90% or higher). In some example, the neural network may output a list of most likely matching patients (e.g., a list of those patients associated with a probability of a match greater than 85%, for example), with the ultimate determination of a match (or no match) being made responsive to confirmatory user input. In some examples, the listing of most likely matching patients may be arranged in order of matching probability.

The process also involves the acquisition of ultrasound images, and specifically real-time imaging, of the patient. Initially, the imaging system (e.g., scanner 12) loads default acquisition settings (as show in block 110), which may be a set of acquisition parameter settings determined (e.g., through optimization and/or in consultation with expert users) to be the preferred settings for a particular imaging mode (e.g., B-mode, M-mode, Doppler, etc.) and/or for a specific clinical imaging application (e.g., cardiac, breast, maternal-fetal imaging, etc.). On most imaging systems, the default acquisition settings are typically further configurable by the sonographer prior to or during the exam. In some embodiments, the default acquisition settings may additionally or alternatively include acquisition settings previously saved by the sonographer on the local device (e.g., scanner 12). In the present scenario, if the system 10 determines that the patient is not a recurring patient (as shown at decision block 114), no automatic adjustment of the acquisition settings is performed and the imaging session continues (from block 112 and as further shown in block 116), with either the default settings or as further manually adjusted by the sonographer. Any images acquired and saved locally (block 124) during the imaging session may subsequently be archived (as shown in block 108) for use in a future imaging session for the automatic retrieval of acquisition settings.

If a determination is made by the system (at block 114) that the patient is a recurring patient, the process continues to the view-matching process (block 118). As illustrated, the scanner 12 is connected (e.g., via a wired or wireless connection) to a source of previously acquired image data. For example, the source of previously acquired image data may include a networked storage device (e.g., remote device 14, which may be part of the medical facility's picture archiving and communication system (PACS)). Upon identification of the patient as a recurring patient, the system 10 retrieves from the source (e.g., device 14) prior image data of the recurring patient, as well as the corresponding image acquisition settings used to acquire the prior image data, as shown in block 106. In some examples, the images, such as when archived to PACS, are stored using a standardized format, such as DICOM, and thus each archived image or sequence of images (e.g., a cineloop) may be accompanied with the corresponding acquisition parameter settings used to acquire the image data. In the case of the DICOM, this information may be stored in the header of the DICOM file. In some specific examples, the prior image data retrieved (with corresponding acquisition settings) may include archived images from the recurring patient's last exam of the same type (e.g., the last breast exam or last liver exam), or a number (2, 3, 4, 5, or more) of the recurring patient's most recent exams of the same type.

The image data files retrieved from the source (e.g., device 14) are used by one or more processors of system 10 to identify a prior image with a view that matches the current image, as described further below. As will be appreciated, the particular anatomical structures shown in any given image, specifically in 2D imaging, will depend on how the view plane (or scan plane) of the probe intersect the tissue being imaged, which will depend on the placement of the ultrasound probe relative to the patient and/or the steering angle of the ultrasound beam. The view matching process in effect determines a probability that any given prior image was taken with the probe oriented and beam directed toward the tissue the same manner as those of the current image, such that measurements of a region of interest, for example measurements of a size of a lesion, may be more accurately performed over time by being taken at the same location. Furthermore, because the acquisition settings affect the image ultimately produced by the system and thus possibly the measurements obtainable from that image, the same or substantially the same acquisition parameters should be used in longitudinal studies. Thus, in accordance with the present disclosure, if a view (or image) matching the current image is found in the prior image data, the acquisition settings associated with that prior matching view are used to reconfigure the scanner 12 and acquire an updated current view (as shown in block 124). In some cases, the imaging session may proceed through an imaging protocol, for example to obtain a predetermined set of views (e.g., standard views for echocardiographic or fetal ultrasound), and at each step of the protocol (i.e. for each view (block 126)), the system 10 may perform view matching and automatic setting retrieval of the acquisition parameters, e.g., as shown in block 118.

In some embodiments, the view matching and system reconfiguration to apply the retrieved settings may occur in the background (e.g., without operator knowledge or involvement). In some such examples, when the system identifies a match (e.g., based on a similarity score exceeding a certain value), an indication of a match found or of the acquisition of an appropriate current view may be provided to the user, for example by a visual (e.g., the activation of light or cursor) or an audible (e.g., the sounding of a beep) indicator. In other embodiments, the system 10 may display a view-matching interface, as shown in block 122, to provide feedback to the sonographer and/or receive further input during the view matching process. For example, the scanner 12 may be configured to concurrently display (e.g., side by side) a pair of images that are being matched at any given moment. In such examples, as the scanner acquires a current (real-time) image, which is displayed, in a matching view interface, concurrently (e.g., side by side) with each of the previous images as they are being processed against the current image (e.g., analyzed by the neural network for the computation of a similarity score). In some embodiments, a measure of similarity between the two displayed images (e.g., a similarity score) may also be displayed along with the pair of images that are being matched. Typically, during the view matching process, the sonographer holds the probe in the same position with respect to the patient to maintain the same view in the current image until a match is found (or no match is confirmed) from the prior images and a new current image with the retrieved prior settings has been captured and locally stored (at block 124). As previously noted, a visual or audible indicator may be provided to inform the sonographer that the matching view has been found and/or that the updated image has been captured. In some embodiments, the indicator may be provided after a matching view has been found and prior settings applied to the scanner, but prior to locally storing the new image with the updated settings, such that the sonographer may have an opportunity to further adjust the image acquisition settings. In such examples, upon the identification of the matching view, the prior settings are retrieved and automatically applied to the scanner so that the sonographer may preview and visually confirm that the two concurrently displayed views are a sufficient match prior to the updated image being stored. After an image has been acquired with the updated settings and locally stored (per block 124), the sonographer may move the probe to acquire another view (block 126).

As discussed, in some embodiments, the system 10 may expect confirmatory operator input during the matching process. For example, the system 10 may enter freeze mode when a matching view has been found for the current image and await confirmatory input that the two views are sufficiently matched before adjusting the settings and/or acquiring further images with the updated settings. Such confirmatory input may be advantageous for subsequent training of the view matching neural net, which is described further herein. In other embodiments however, the system may not enter freeze mode but may instead automatically store the current image upon the identification of a matching prior view. As described further below, a neural network may be trained such that given any pair of images and settings (I1, S1) and (I2, S2) as inputs, the neural networks determines whether the pair of images are from the same view, regardless of any impact that the settings may have on the perceivable (by the human eye) similarities of the pairs of images. Quantitative measurements may be performed at any time during the imaging session, for example after a matching view has been found and the settings updated, the operator may enter freeze mode following the acquisition of the updated current image to perform measurements on the updated image.

Any of the locally stored images, identified matching image pairs, and corresponding settings obtained by the scanner during a given imaging session may be archived to a networked storage device (e.g., on remote computing device 14), for example for use in longitudinal studies of the same patient and/or subsequent training of one or more of the neural networks employed by the system. The acquisition settings associated with each image to be archived may be stored with the image data (e.g., in the header of a standard file format such as DICOM) or in a table or database (e.g., tables 132 and 134). In some examples, a table associating the acquisition settings of each image with a unique identifier for that image may be generated and stored on the device 14. The types of acquisition settings that may be included in the stored settings may include for example, transmit settings such as transmit power, depth, focus, frequency option, harmonic, Doppler scale, or any other transmit setting, receive settings such as 2D Gain, time gain compensation (TGC) curve, line density, and other receive settings, signal and image processing settings such as XRes settings, compression dynamic range, colormap, or others or any combinations thereof. At the end of the imaging session (or intermittently during the imaging session), images locally saved on the scanner 12 may be transmitted to the remote storage device. The newly acquired images and settings may be formatted similarly to the remaining entries in the database of prior image data so they can be appended thereto for future use in automatic reconfiguring of the scanner 12 during a subsequent imaging session. Additionally, pairs of matching views, each including a current and prior matching view image, may be saved for example in a matching views database 132, which may facilitate queries by a radiologist in a subsequent exam and/or additional training of the view matching neural network. In some examples, entries in the matching views database may be organized in tables containing columns of matching view pairs, with each column being associated with a unique pair of matching views.

Figure 2:
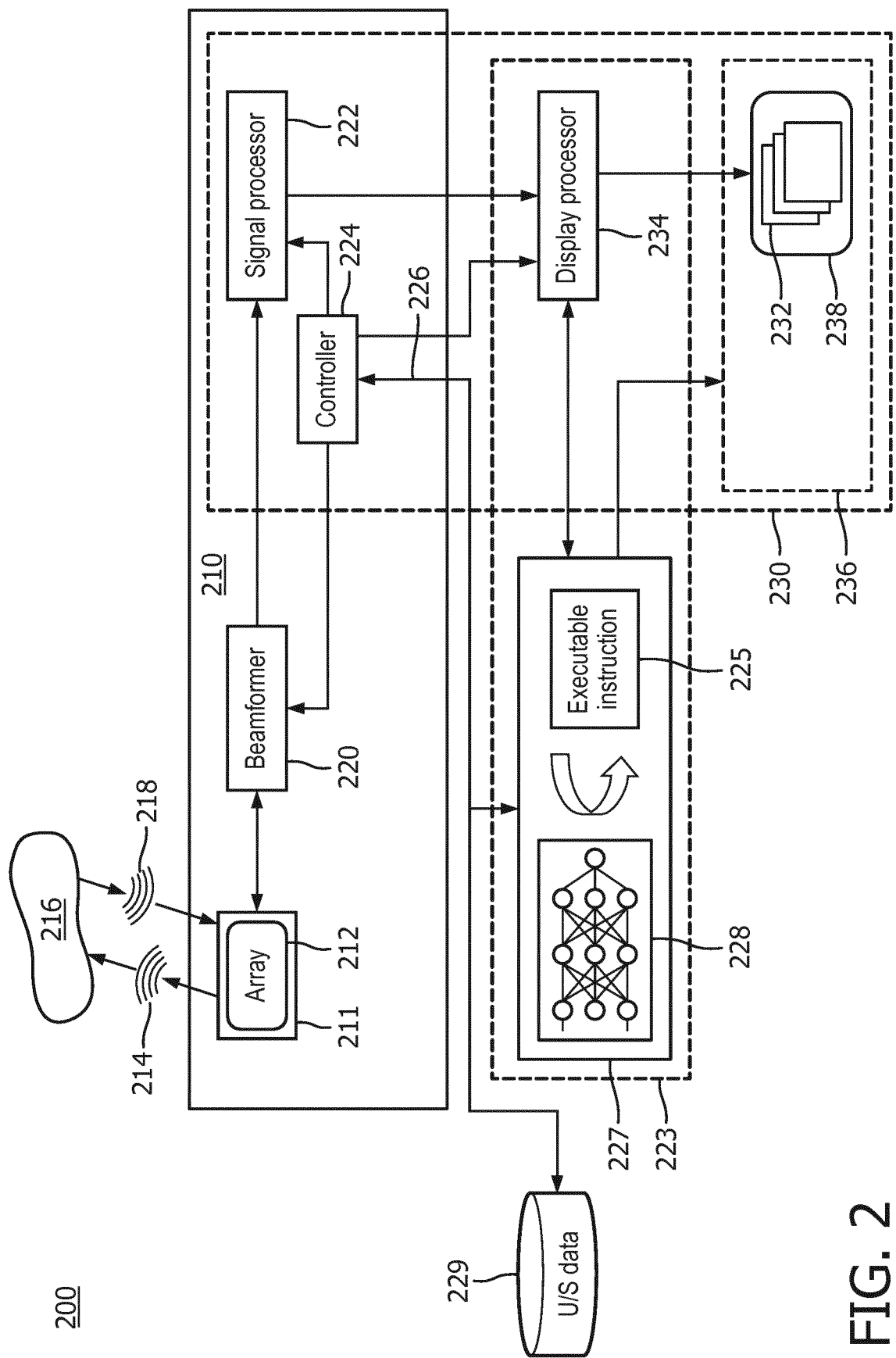
FIG. 2 is a block diagram of a system according to the some examples of the present disclosure.

An ultrasound imaging system in accordance with some embodiments may include ultrasound probe and a processor communicatively coupled to the ultrasound probe and to a source of previously-acquired ultrasound image data. FIG. 2 shows a block diagram of a system 200 in accordance with principles of the present invention. The ultrasound system 200 includes an ultrasound data acquisition unit 210. Components of the system 200 may be used to implement at least part of the system 10 in FIG. 1, for example the ultrasound scanner 12. The system 200 includes an ultrasound data acquisition unit 210, a settings retrieval engine 227 implementing a neural network 228 trained to identify matching pairs of images and connected to a source of previously acquired ultrasound data 229. The components of system 200 and arrangement thereof in FIG. 2 are illustrative only and variations, such as combining, rearranging, adding, or removing components are contemplated.

The ultrasound data acquisition unit 210 may be configured to acquire ultrasound image data and display the ultrasound image data in real-time (i.e., as the image data is being acquired). The ultrasound data acquisition unit 210 may include some or all of the components of a typical ultrasound scanner. For example, the ultrasound data acquisition unit 210 may include an ultrasound transducer or probe 211, which includes an ultrasound sensor array 212 configured to transmit ultrasound 214 toward a target region 216, e.g., breast tissue, abdomen, or other biological tissue of a subject, and detect echoes 218 responsive to the ultrasound. The ultrasound data acquisition unit 210 may further include a beamformer 220 and a signal processor 222, which may be configured to generate the ultrasound image data 232, which may be displayed in one or more ultrasound image frames in real-time, from the echoes 218 detected by the array 212. The beamformer 220 may include one or more beamformers, (e.g., a microbeamformer in combination with a main beamformer in the ultrasound system base, or a combination of transmit and receive microbeamformers and/or main beamformers). The beamformer 220 may be configured to control the transmission of ultrasound and reception of echo signals. In some embodiments, the beamformer 220 may include a microbeamformer, which may be co-located with the ultrasound array in the probe, and operating on groups of sensor elements for the transmission and/or reception of signals by the groups of sensor elements of the ultrasound sensor array 212.

In some examples, the signal processor 222 may be housed with the sensor array 212 or it may be physically separate from but communicatively (e.g., via a wired or wireless connection) coupled thereto. The ultrasound data acquisition unit 210 may include or be operatively coupled to a user interface 236, which may be physically connected to a system base 230 that houses the signal processor 222. The user interface 236 may include a display 238 for displaying the ultrasound image data 232 generated responsive to signal processor 222. The signal processor 222 may be communicatively, operatively, and/or physically coupled with the sensor array 212 and/or the beamformer 220. In the example shown in FIG. 2, the signal processor 222 is included as an integral component of the data acquisition unit 210, but in other examples, the signal processor 222 may be a separate component. The signal processor 222 may be configured to receive unfiltered and disorganized ultrasound data embodying the ultrasound echoes 218 received at the sensor array 212. From this data, the signal processor 222 may generate the ultrasound image data 232, e.g., in real-time as an operator ultrasonically scans the region 216, which may then be displayed responsive to display processor 234 on the display 238.

The ultrasound data acquisition unit 210 may include a controller 224, which may be configured to set imaging parameters of the system 200, e.g., to control the transmission and reception of signals by the array 212, as well as certain signal and image processing functions of the system 200. The controller 224 may be communicatively coupled to the settings retrieval engine 227 for the automatic setting of imaging parameters as described herein. The controller 224 may be configured to set imaging parameters in accordance with pre-stored settings (also referred to as pre-sets), which may be stored in memory of the ultrasound data acquisition unit 210, and may be further configured to adjust the settings e.g., responsive to user input or to input(s) provided from the settings retrieval engine 227.

In some examples, the imaging parameters of the system 200 may be adjusted by the controller 224 in accordance with settings 226 retrieved from a source of previously-acquired ultrasound image data 229, these settings 226 also referred to as previous settings 226. The previous settings 226 may be automatically applied in some cases upon the occurrence of a condition (e.g., a determination of a match between the current and a previously acquired image). The settings applied by controller 224 may be utilized by the beamformer 220 in controlling the excitation of elements of the array for the transmission and detection of signals by the array 212. Settings applied by controller 224 may also affect the signal and image processing of acquired ultrasound data, e.g., by controlling compressed dynamic range for display of images, or other image processing or display settings.

The data acquisition unit 210 may be communicatively connected to at least one processor 223 configured to perform one or more of the functions associated with the automatic retrieval and application of imaging settings. The processor 223 may include a settings retrieval engine 227 and may be coupled to a source of previously-acquired ultrasound image data 229. The source of previously-acquired ultrasound image data 229 may include a storage device (e.g., one or more hard disk drives, solid state drives, or any other type of suitable storage device comprising non-volatile memory) communicatively connected (via a wired or wireless connection) to the processor 223. The processor 223 may include one or more processing units (e.g., one or more single or multi-core CPUs, a single GPU or GPU cluster, or any arrangement of multiple processors configured for example for parallel processing) and uniquely configured to perform the functions described herein. As described with reference to FIG. 1, the processor 223 may be configured to receive patient identification information (e.g., responsive to user input and/or supplemented by additional information such a photo of the patient) and to determine whether the patient identification information identifies a recurring patient. In some embodiments, the processor 223 may employ a neural network trained to determine whether the patient identification information, even if noisy, corresponds to another patient record within a patient database and thus make determination of whether the patient is a recurring patient. The processor 223 may be further configured, upon a determination that the patient identification information identifies a recurring patient, to cause the system 200 to retrieve, from the source 229, previously-acquired ultrasound images (also referred to as previous images) associated with the recurring patient.

The processor 223 may be further configured to generate a current ultrasound image and cause the current ultrasound image to be displayed. In some examples, system 200 may include a display processor 234, which controls the information displayed on the display 238. The display processor 234 generates the images and the manner in which they are displayed based on the information received from the signal processor 222 and information received from processor the settings retrieval engine 227. The display processor 234 may generate image displays uniquely associated with the operation of settings retrieval engine 227, for example the concurrent display of image pairs including the current ultrasound image and one or more of the previously acquired images, which may be analyzed by the settings retrieval engine 227 against the current image for a possible match. The display processor 234 may also generate a variety of other graphical user interface elements including graphical overlays (e.g., information, indicators, and the like) that may be displayed with the ultrasound image data and/or a variety of interactive GUI elements such as input boxes, icons, and other type of user controls. For example, the display processor 234 may generate a match or similarity indicator, e.g., which may be provided as a graphical representation (alpha-numeric, color-coded, or other) of a similarity score of the pair of images (see e.g., FIG. 5).

In accordance with the principles of the present disclosure, the processor 223 may apply a neural network 228 to the current ultrasound image produced based on echoes detected by array 212 and the previous ultrasound images retrieved from source 229 to identify a matching pair of images.

To that end, the processor 223 may include a settings retrieval engine 227. The settings retrieval engine 227 may be implemented in any suitable combination of hard-wired circuitry (e.g., one or more application specific integrated circuits ASICs) and software (e.g., executable instructions 225, which may be performed by a processor 228). The executable instructions 225 may be stored in memory of the system 200 (either in the form of source code or compiled/machine code) and may be executed by processor 223 to perform the automatic retrieval and setting of imaging parameters described herein. The setting retrieval engine 227 may be implemented in a single or multi-core CPU, a single GPU or GPU cluster, or any arrangement of multiple processors configured for example for parallel processing, and specifically programmed by the executable instructions 225 to execute a neural network algorithm in accordance with the examples herein, e.g., a neural network 228 trained to identify, from a set of previously acquired and stored ultrasound images, a matching ultrasound image to any new/current image acquired (e.g., in real-time) by the data acquisition unit 210.

In operation, the processor 223 may provide, for each of a plurality of the previous ultrasound images retrieved from the source 229, a pair of ultrasound images that includes the current ultrasound image and one of the plurality of previous ultrasound images to the neural network 228. As described, although the same imaging view of a subject may be represented in two images by different pixel data (e.g., due to different imaging settings), the neural network 228 may be trained to recognize a match irrespective of the differences in the pixel data, for example by converting the image data (and, in some cases, the associated imaging settings) to one or more features vectors which are then analyzed for similarities. Multiple known pairs of images and optionally settings may be used to train the neural network to derive a descriptive and/or similarity function as may be suitable for determining whether the pair of images represent the same imaging view or plane through the biological tissue of any given patient.

Figure 5:
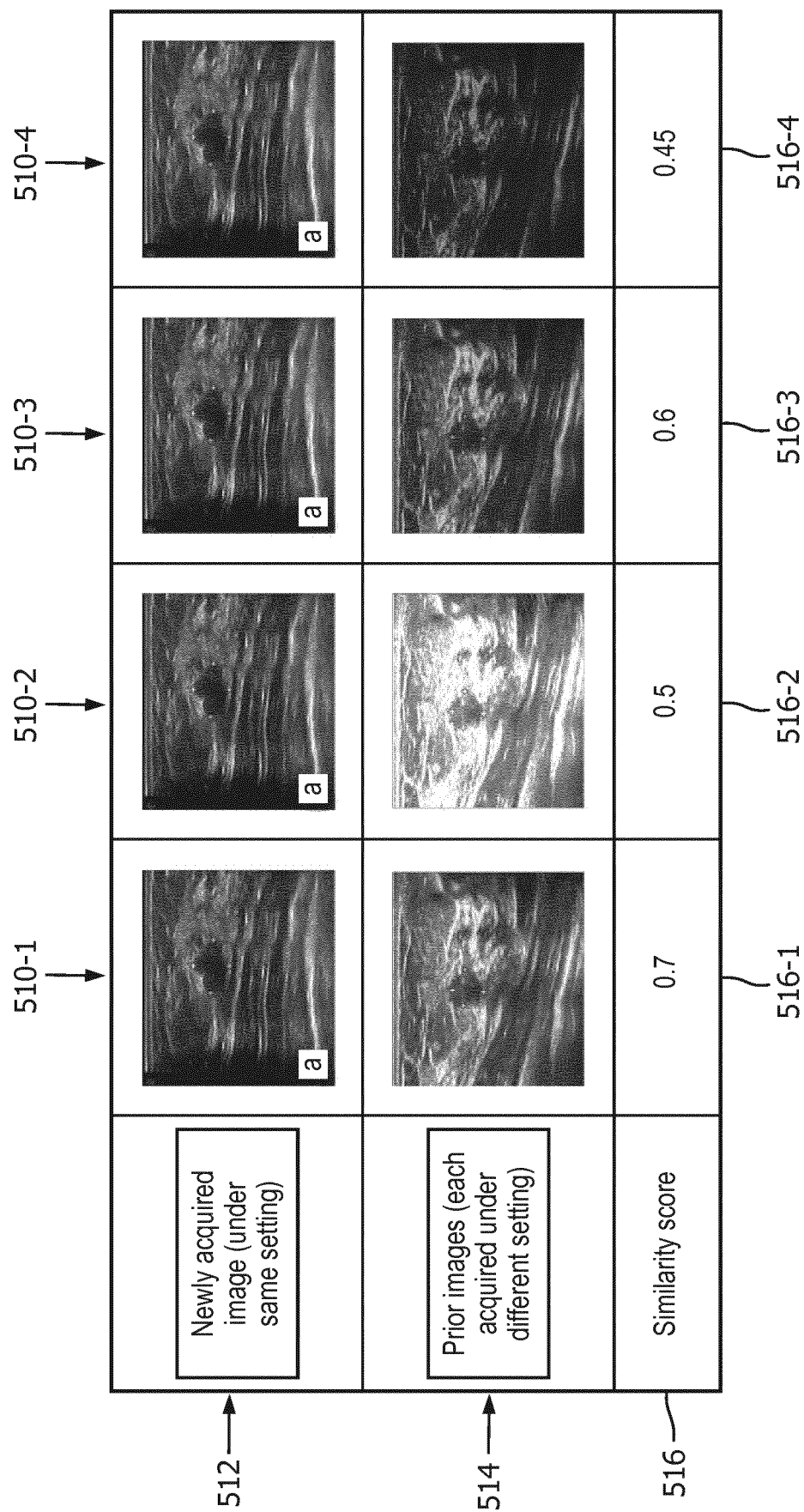
FIG. 5 illustrates example pairs of ultrasound images of a same region of interest with a similarity score computed by a neural network according to the present disclosure.

In some examples, and as described further below, the neural network 228 may be trained to compute a similarity score (see e.g., image pairs 510-1 through 510-4 with corresponding similarity scores 516-1 through 516-4 in FIG. 5) for each of a plurality of input image pairs (e.g., image pairs of current 512 and previous 514 images shown in FIG. 5). In some embodiments, the neural network 228 may include one or more neural networks (or machine learning models or algorithms) and/or additional computational modules operatively arranged to determine whether the input images match or do not match. In some examples, a plurality of neural networks each having the same or similar architecture, may be used to implement the neural network 228. The neural network 228 may be trained to match images in any of a variety of different clinical/imaging applications (e.g., cardiac, fetal, lung, or breast ultrasound). In other examples, dedicated neural network models may be trained for each clinical application and intelligently automatically selected based on the specific application that the data acquisition unit 210 is imaging at a given time.

In some embodiments, the neural network may include at least one neural network, which may be configured to covert the input images, and in some cases in combination with the corresponding imaging settings, to respective feature vectors. For example, the neural network may be a deep neural network including a pair of branches, each comprising a neural network (e.g., a convolutional neural network) and operating in parallel to process each of the images in the pair and output a feature factor describing each of the images in the pair. The feature vectors may then be compared (e.g., by computing a distance metric, as described further below) to determine a similarity or match between the two images. The term match as used herein is meant to imply an ultimate determination of a matching view (whether or not based on a computed similarity), while the term similarity is generally used to refer to some form of an assessment of the similarity between two images, whether or not ultimately determined to constitute a match. For example, the neural network 228 may output a similarity score for any given pair of images and/or may additionally automatically output determination of a match if the similarity score exceed a certain value (e.g., a similarity score greater than 0.7 on a normalized scale of 0 to 1). In other examples, the neural network 228 may not output any intermediate information (e.g., a similarity score) but may be configured simply to determine if there is a match or no match, and if a match is found to proceed to the automatic settings of parameters or if no match if found to continue searching through the database of previous images. In yet other examples, the settings retrieval engine 227 may receive as output a set of image pairs and accompanying similarity scores. The set of image pairs may be a small subset (e.g., 3, 4, 5, or more) from the full plurality of image pairs analyzed by the neural network 228 and determined to constitute the closest matching pairs, which may then be displayed, responsive to commands from processor 223, to the user in pairs along with their corresponding similarity score (e.g., as shown in FIG. 5). Upon receipt of confirmatory user input by the system 200, the controller 224 may then proceed to adjust the imaging parameters in accordance with the selected one of the image pairs from the subset and/or in accordance with further manual inputs/adjustments.

Upon a determination that a given pair of images correspond to a matching pair, the processor 223, or more specifically the settings retrieval engine 227, may automatically communicate the imaging settings associated with the previously-acquired image (i.e. the settings used to acquire the image) of the given pair to the data acquisition unit 210, or more specifically to the controller 224, which then automatically sets the imaging parameters of the system 200 to correspond to those of the matching previously-acquired image. The process of transmitting the previous settings and the applying of the previous settings to the system may occur automatically (e.g., without operator knowledge or involvement) and thus subsequently acquired images may automatically reflect the same imaging settings and thus be likely to more accurately represent the bodily structure in a subsequent current image facilitating more accurate measurements and diagnosis. Moreover, the exam workflow may thus be improved in that the sonographer need not perform manual adjustments for every view to be acquired as the system 200 automatically (in some cases substantially or entirely in the background) performs the automatic acquisition and setting of imaging parameters.

Figure 3A:
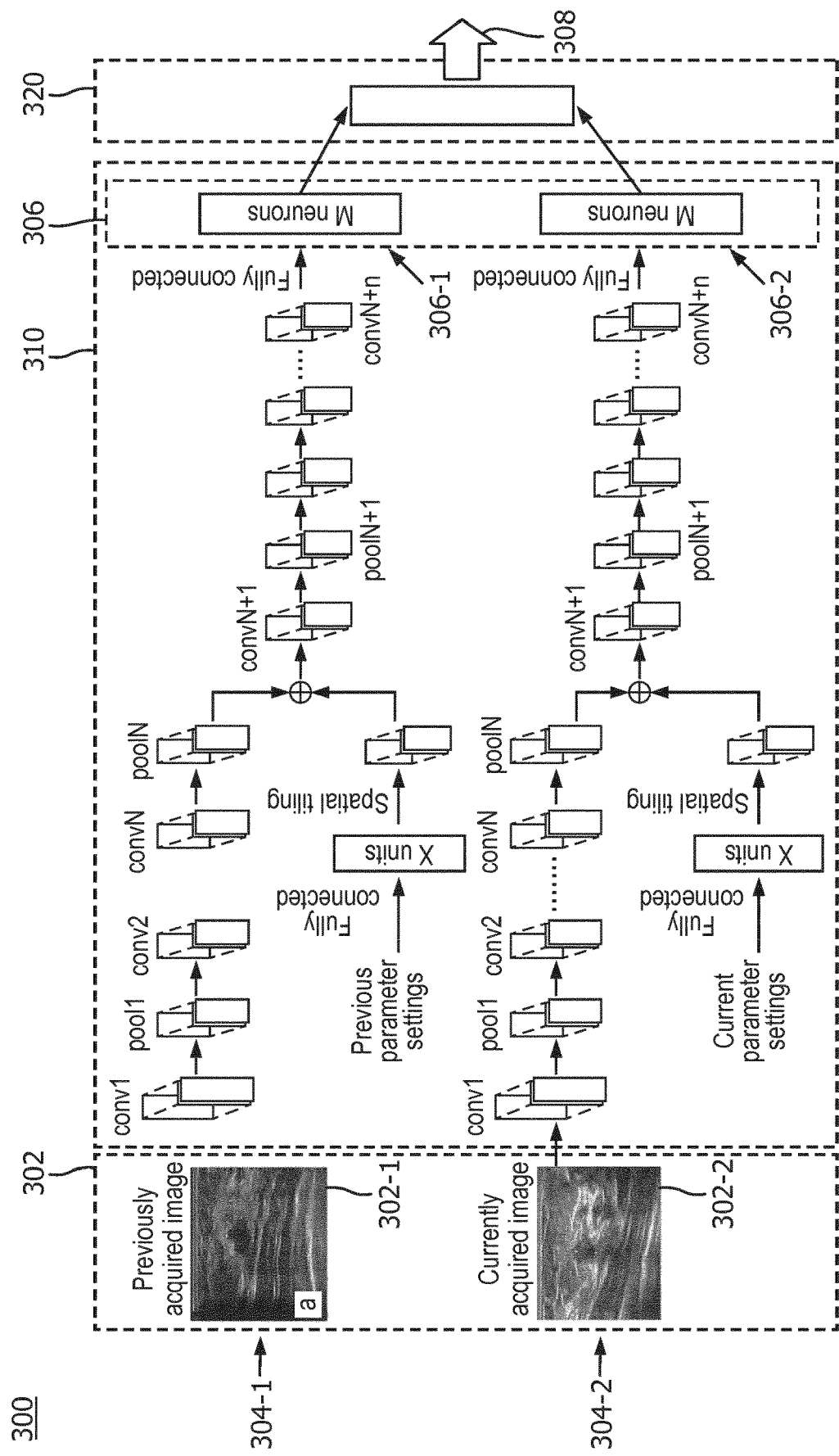
FIG. 3A shows a block diagram of an artificial neural network trained to identify pairs of matching images in accordance with some examples herein.
Figure 3B:
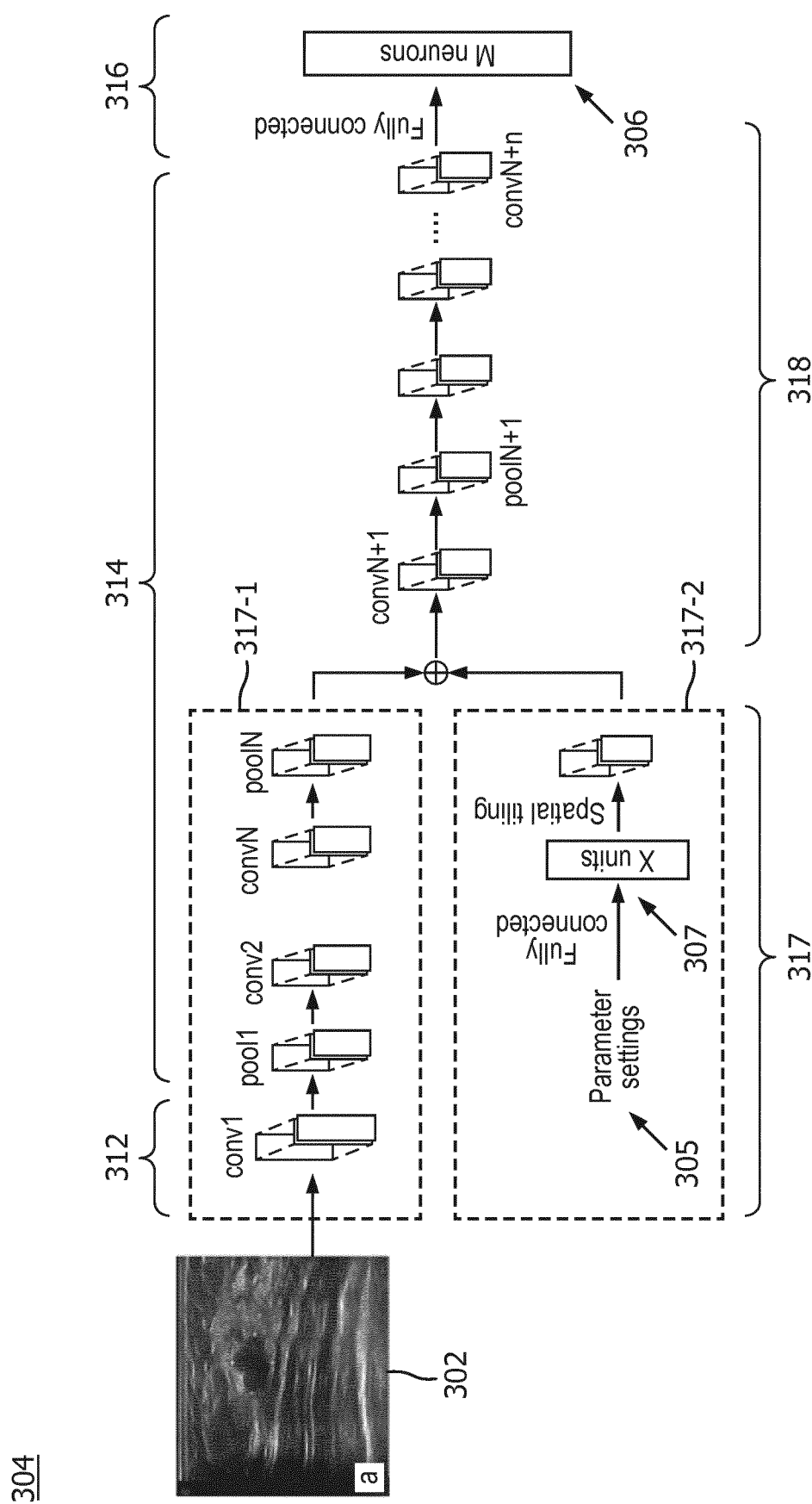
FIG. 3B shows a portion of the neural network in FIG. 3A.

With the increasing volume of stored medical image data (e.g., in PACS or in cloud storage), the availability of high-quality clinical images is increasing, which may be leveraged to train a neural network to learn a similarity function from known pairs of matching and non-matching images. For example, a deep neural network, such as a convolutional neural network may be trained to learn a similarity function from training datasets that include multiple (hundreds often thousands or even more) annotated/labeled image pairs, also referred to as training image pairs. It will be understood that the training image pairs need not include full images produced by an imagining system but may include patches or portions of images of the same target biological tissue or organ. FIGS. 3A and 3B show aspects of an architecture of an example neural network in accordance with the principles of the present invention. The neural network 300 in FIG. 3A is a deep neural network, and includes more specifically at least one Convolutional Neural Network (CNN). In some embodiments, the neural network 300 may include one, two, or more neural networks arranged operatively to produce the desired result, in this case to make a determination of whether the views of the two images in a pair of input images match. While the exact content of the image data presented in each image (e.g., the array of pixel values displayed as the first and second image) would likely differ in most instances, the neural network 300 is trained to make a determination of whether the view (that is, the scan plane or location within the subject at which the image is take) in each image is the same in both images.

In the specific illustrated example of FIG. 3A, the neural network 300 includes a first sub-network or portion 310 and a second sub-network or portion 310. The first portion 310 operates on the image pair as input and outputs a pair of feature vectors 306, which may be thought of as descriptors of the features in the input image. The second portion 320, receives the output of the first portion 310 (e.g., feature vectors 306-1 and 306-2) and computes a similarity between the two feature vectors and/or makes a final determination of whether the two input images match. The output 308 of the neural network 300 is used by the ultrasound imaging system to control further operation and/or trigger further processing steps of the ultrasound imaging system. The first portion 310, the second portion 320, or both, may individually be comprised of one or more layers of interconnected neural nodes and may thus individually be referred to as a neural network or sub-network. The term interconnected in the context herein does not necessarily imply that all nodes are fully connected but simply implies that one or more nodes of a given layer of the network is connected to one or more nodes of another layer of the network. In some examples, the functionality of at least one of the portions 310 and 320, or a component thereof, may be performed by a pre-programmed computational module (i.e., a non-machine learning based algorithm). This computational module may be combined with at least one neural network to define the neural network 300. It will also be understood that the specific architecture of the neural network 300 in FIG. 3A is exemplary only and that other architectures and arrangement of layers or components may be used in other examples.

Referring now also to FIG. 3B, the first portion 310 of neural network 300 includes two branches 304-1 and 304-2, which operate in parallel. Each of the branches 304-1 and 304-2 may itself constitute a deep neural network (e.g., a CNN). In the specific example, each of the branches 304-1 and 304-2 includes a plurality of neural layers including one or more convolutional, pooling, and fully connected layers. In this example, each of the two branches 304-1 and 304-2 of network 300 has the same architecture and weights. Each branch operates on one of the images of the input image pair 302 to produce a descriptor (e.g., an M-sized feature vector 306-1 or 306-2) of the input image, which are subsequently compared to determine the similarity between the two input images (302-1 and 302-1). As described in input image pair 302 includes a first image 302-1, which is a previously acquired image and a second image 302-2, which is the currently acquired image (e.g., real-time image produced by the imaging device). The example two-branch architecture of network 300 enables the network 300 to simultaneously operate on both of the input images; however, it will be appreciated that in other examples a different architecture may be used, for example, an architecture where the input images are analyzed in sequence to arrive at the corresponding descriptor and the descriptors are then similarly compared as described herein.

Figure 4:
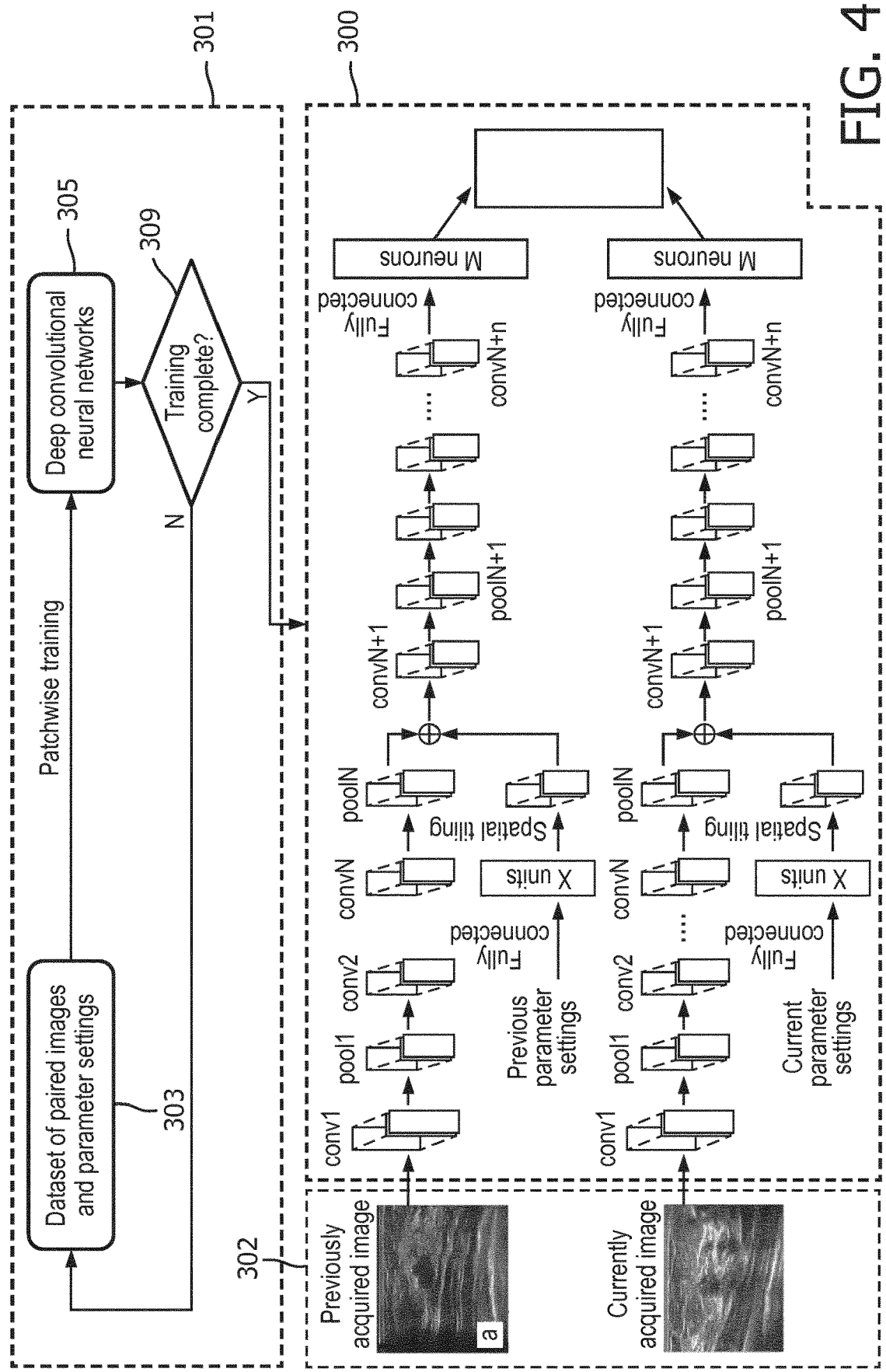
FIG. 4 shows a neural network and training thereof in accordance with some examples herein.

Referring also to FIG. 4, the neural network 300 may be trained (e.g., via a training process 301) by providing the network-in-training 305 with multiple sets (tens, hundreds, thousands or more) of training data 303 (e.g., known image pairs and their corresponding settings). The first portion of the network learns through training a descriptor function and when trained is capable of producing a descriptor (or feature vector) for any input image, while the similarity portion learns a similarity function and is capable of comparing pairs of descriptors to determine their similarity. In this parallel model architecture, the two branches are trained together, for example through standard backpropagation. That is, during training, the parameters (e.g., weights) of the two branches are updated at the same time until convergence or sufficient minimization of a cumulative cost function. As shown in training block 301, to train the neural network 300, training data 303 may be provided to one or more neural networks in training 305 (e.g., prior deployment of the network for patient examination), although in some cases further training may occur after the network 300 has been deployed on an ultrasound imaging system. As described, such in-the-field training may be performed using image data and labeling acquired from one or more patient exams. The number of training data sets, as well as various parameters of the network 300 may be different and tailored depending on the complexity of the task (e.g., the number of different features to be trained, which may be significantly greater if training the network to match images and thus learn features associated with different clinical applications). Training may be patchwise (e.g. using portions of an image or imaged area) or using full images of a particular anatomical side. Training may involve using 2D or 3D image data. The network 300 may be trained to determine the similarity and thus match images for multiple clinical applications (e.g., cardiac, breast, lung ultrasound) or multiple individual networks having similar architecture as the network 300 may be communicatively coupled to and appropriately invoked by the imaging device (scanner 12) based on the specific clinical application.

As shown in FIG. 3B, each branch of neural network 300 may implement a sub-network, in this case a convolutional neural network 304. The branch or sub-network 304 of this examples includes a plurality of layers 312, 314, 316 including one or more convolutional layers (e.g., in this case N+n Conv layers), pooling layers, and fully connected layers. In examples of the network 300, the sub-network 304 may include any number of layers depending on the complexity of the task. The input layer 312 of network 304 is a convolutional layer and the output layer 316 is a fully connected layer, with the intermediate layers 314 including a series of convolutional layers, each of which may include at least one of a convolutional, non-linear regularization, batch normalization, and spatial pooling layers. The input to the network 304 is an image and associated (or corresponding) acquisition settings 305. The output 306 of the network 304 (e.g., from the last fully connected layer) is an M-sized feature vector. The parameters of the network (e.g., the total number of layers (N+n) and/or the size of the output may depend upon the complexity of the task (e.g., the sizes of the input, the number of features that the network is to be trained to learn), the computational resources available, and other design parameters.

In the first convolutional layer (Conv1), one or more filters are applied or convolved over the input image 302, for example the previously acquired image 302-1) to produce a stack of feature (or activation) maps, and after a spatial pooling operation, each having a size smaller than that of the original (input) image and being dependent upon the size (or receptive field) of the filters and the step size (or stride) of the pooling operation. Each feature map in the stack may be represented by a 2D array of values (in the case of a single channel input, or a 3D array in the case of a multi-channel, for example an RGB image input). The stack of feature maps (or output volume) from Conv1 layer is then provided to the second convolutional layer (Conv2), e.g., after batch normalization, non-linear regularization, and pooling, to produce another set of feature maps, which are again provided to the next convolutional layer (e.g., after non-linear regularization, batch normalization, and pooling) and so on, until a set of feature maps (or output volume) of a desired size is produced by the last convolutional layer (ConvN layer) of the first part 317 of network 304 (e.g., as shown in block 317-1).

In parallel, as shown in block 317-2, the network 304 also receives, as input, the parameter settings 305 associated with the input image 302. These parameter settings 305 are provided to the network 304 as a X dimensional vector 307 input, also referred to as settings vector 307, which contains X number of values, each corresponding to the setting for each of a plurality of unique ultrasound imaging parameters (e.g., gain, TGC, focal zone, frequency, dynamic range, etc.). The settings vector 307 is the same size as one of the dimensions of the features maps produced at the N convolutional layer, such that the settings vector 307 may be piece-wise added to each feature map produced at the layer N. The number of convolutions in the block 317-1 may thus depend upon the desired size of the feature map at the end of the last convolution layer, which may be driven by the size of the second input—i.e., the settings vector 307.

In some examples, the settings vector 307 may be spatially tiled, i.e., to replicate it over the other spatial dimension of the feature map output at layer N. That is, the spatial tiling layer takes the X-sized vector and outputs an X by Z array in which each of the columns Z contains the same values of the original settings vector. The output of block 317-1 (e.g., X by Z feature maps produced at layer N) and the output of block 317-2 (X by Z array produced by spatially tiling vector 307) may then be combined (e.g., by adding, element by element, the values of the array output at block 317-2 to the values of each of the feature maps output at block 317-1). The output of the summation block is provided to the first convolutional layer (ConvN+1) of the second part 318 of network 304. The feature maps are processed through another set of convolutional layers, each of which may include a non-linear regularization, batch normalization, and pooling to produce the final set of feature maps (or output volume), which is then provided to the fully connected layer for computing the M-sized feature vector 306.

As previously described, the network 304 may represent only one of the branches of the larger neural network employed to determine a similarity between a pair of input images. Thus, a similar network as the network 304 may be applied to the other input image (e.g., currently acquired image 302-2) to produce a feature vector 306-2. The features vectors output by each of the branches of network 300 are then compared to determine a similarity between the input images (e.g., compute a similarity score). For example, the pair of feature vectors may be compared by measuring their distance at a certain metric space, e.g. squared difference, correlation analysis or other statistical metrics. The similarity score represents this distance metric. During training, a cost function may be minimized to train the system to identify matching and non-matching pairs. The cost function is defined on the principle that for matching (or same view) images, the distance metric is minimized, while for non-matching (or different views) images, the distance metric moves in the opposite direction towards maximizing the distance metric. A trained network 300 may therefore be able to compute a distance metric, and from that determine a similarity score, which is inversely related to the distance metric (i.e., the smaller the distance metric the greater the similarity score). A threshold may be utilized to determine the distance metric (or inversely the similarity score) outputs that correspond to matching pairs and non-matching pairs.

Referring back to FIG. 3A, the output of the two branches (i.e., the pair of feature vectors 312-1, 312-2) is provided to a similarity determination module 310, which provides an output 311. For example, the similarity determination module 310 compares the feature vectors to output either a binary determination (e.g., computes a value of 1 for match and 0 for no-match) or to compute a similarity score (e.g., some non-integer value between 0 and 1. The module 310, may provide as the output 311 either the computed value or determination of match/no-match, which may be used to generate one or more indicators on a display of the ultrasound system, and/or trigger additional data retrieval and/or processing steps as described herein.

In some examples, the similarity determination module 310 may compute the similarity score using a distance function (e.g., a Euclidean distance function $L^2$ norm). For example, for an M dimensional space, the Euclidean distance may be computed using the function:

$$d(p, q) = \sqrt{(p_1 - q_1)^2 + (p_2 - q_2)^2 + \cdots + (p_i - q_i)^2 + \cdots + (p_m - q_m)^2},$$

where d is the Euclidean distance between the two points p and q or in this example, the distance between the values of the M-sized feature vector 312-1 and the M-sized feature vector 312-2. The module 310 may be configured to output a determination of a match (e.g., an output of 1) if the computed distance does not exceed a predetermined value and a determination of no match (e.g., an output of 0) if the computed distance is equal to or exceed the predetermined value.

In other examples, a neural network (e.g., applying a discriminative model) may be trained to perform the final determination of match or no match. That is, in some embodiments, the similarity determination module 310 may apply yet another neural network trained to derive a similarity score and/or make the binary determination (match or no match). This neural network may, for example, implement a discriminative model trained to classify pairs of feature vectors into similarity categories, such as two categories corresponding to 0 and 1, or a plurality of categories (e.g., 0, 0.05, 0.1, 0.15, 0.2, etc.) or any number of intermediate similarity score values between 0 and 1). To train the neural network, known pairs of feature vectors may be provided to the network as training data. That is, the neural network may be provided training data including multiple labeled input sets (I(x, y), label), where x and y are the two feature vectors and label is the known classification or category (e.g., a value of 0 or 1 for training a binary classification, or some non-integer value between 0 and 1) such that the network may learn a probability function, e.g., the conditional probability distribution p(label|I), that is, the probability of a category label (e.g., 0 or 1 in the binary scenario) given an input pair I of feature vectors x and y.

Figure 6:
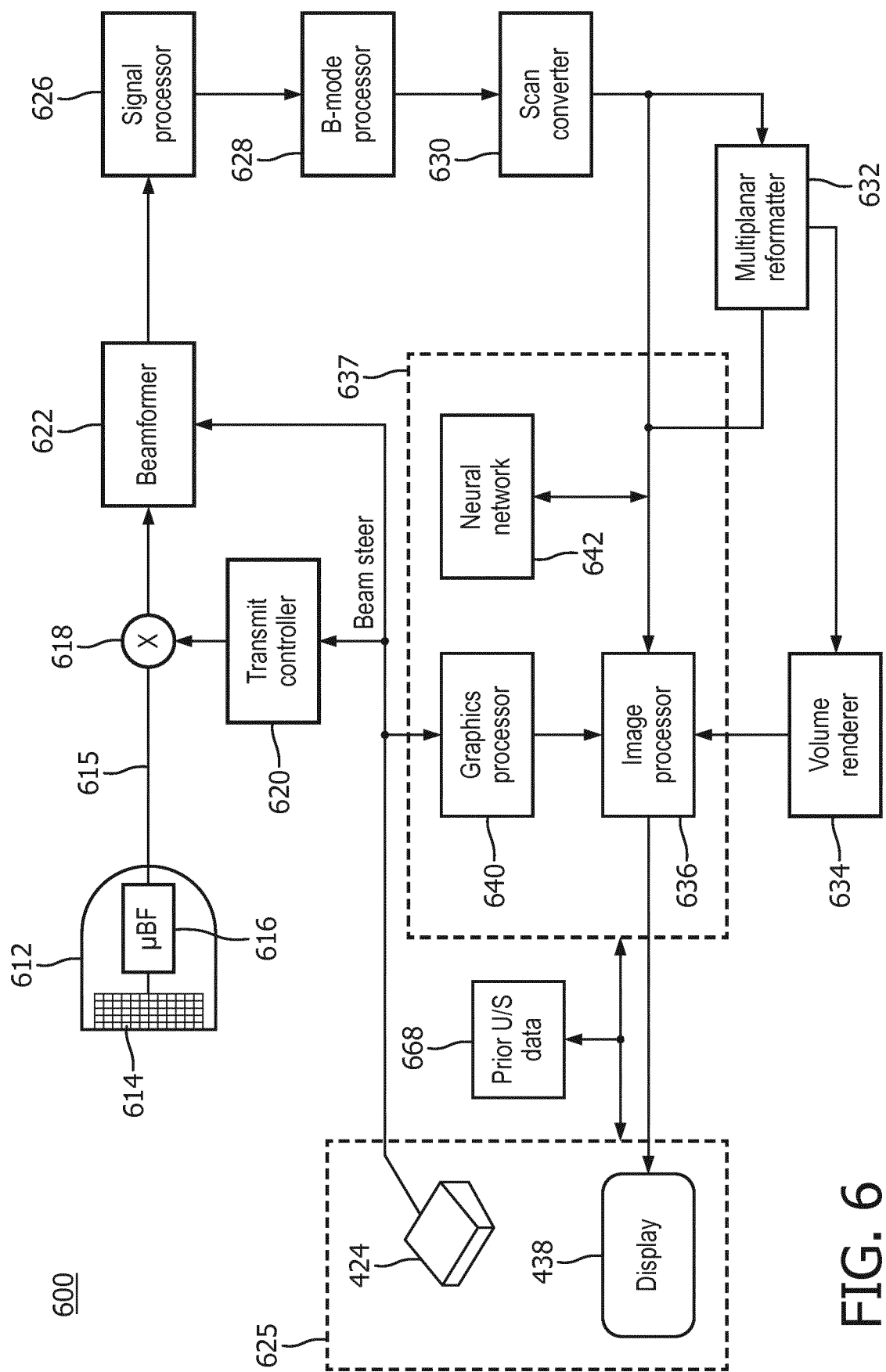
FIG. 6 shows a block diagram of an ultrasound imaging system according to further examples of the present disclosure.

FIG. 6 shows a block diagram of an ultrasound imaging system constructed in accordance with the principles of the present disclosure. Some or all of the components of ultrasound imaging system 610 may be used to implement ultrasound imaging systems in accordance with any of the examples herein, for example system 200 in FIG. 2. The ultrasound imaging system 610 in FIG. 6 includes ultrasound probe 612, transducer array 614, beamformer 622 and optionally microbeamformer 616, transmit/receive (T/R) switch 618, transmit/receive controller 620, and one or more processing components for generating ultrasound images from echoes detected by the array 614. For example, the system 610 may include signal processor 626, B-mode processor 628, scan converter 630, multiplanar reformatter 632, volume renderer 634, image processor 636, and a graphics processor 640. The system may also include user interface 625, which may include one or more input devices 652, and one or more output device 638. The components shown in FIG. 6 are merely illustrative, and other variations, including eliminating components, combining components, rearranging components, and substituting components are all contemplated.

As shown, the ultrasound imaging system 610 includes an ultrasound probe 612, which includes a transducer array 614 for transmitting ultrasound waves and receiving echo information. A variety of transducer arrays may be used, e.g., linear arrays, curved arrays, or phased arrays. The transducer array 614, for example, can include a two dimensional array (as shown) of transducer elements capable of scanning in both elevation and azimuth dimensions for 2D and/or 3D imaging. The transducer array 614 may be coupled to a microbeamformer 616, which may be located in the ultrasound probe 612. The microbeamformer 616 controls transmission and reception of signals by the transducer elements in the array 614. In the illustrated example, the microbeamformer 616 is coupled to a transmit/receive (T/R) switch 618, which switches between transmission and reception and protects the main beamformer 622 from high energy transmit signals. In some embodiments, for example in portable ultrasound systems, the T/R switch 618 and other elements in the system can be included in the ultrasound probe 612 rather than in a separate ultrasound system base. The ultrasound system base typically includes software and hardware components including circuitry for signal processing and image data generation as well as executable instructions for providing a user interface. In some embodiments, the ultrasound probe 612 may be coupled to the ultrasound system base via a wireless connection (e.g., WiFi, Bluetooth) or via a wired connection (e.g., a probe cable, which may be configured for parallel or serial data transmission).

The transmission of ultrasonic pulses from the transducer array 614 under control of the microbeamformer 616 is directed by the transmit/receive controller 620, which may be coupled to the T/R switch 618 and/or the beamformer 622, which may receive input from the user's operation of a user interface 625. The user interface 625 may include one or more input devices 652 such as on a control panel, which may include one or more mechanical controls (e.g., buttons, encoders, etc.), touch-sensitive controls (e.g., a trackpad, a touchscreen, or the like), and other currently known and later developed input devices (e.g., a touchless/gesture-based interface). The user interface 652 may include one or more output device (e.g., a display 638), configured to provide feedback to the user including the displaying of ultrasound images.

Another function, which may be controlled by the controller 620, is the direction in which beams are steered. Beams may be steered straight ahead from (orthogonal to) the transducer array 614, or at different angles for a wider field of view. The partially beamformed signals produced by the microbeamformer 616 are coupled to a main beamformer 622 where partially beamformed signals from individual patches of transducer elements are combined into a fully beamformed signal. The beamformed signals are coupled to a signal processor 626.

The signal processor 626 can process the received echo signals in various ways, such as bandpass filtering, decimation, I and Q component separation, and harmonic signal separation. The signal processor 626 may also perform additional signal enhancement such as speckle reduction, signal compounding, and noise elimination. The processed signals may be coupled to a B-mode processor 628 for producing B-mode image data. The B-mode processor can employ amplitude detection for the imaging of structures in the body. The signals produced by the B-mode processor 628 may be coupled to a scan converter 630 and a multiplanar reformatter 632. The scan converter 630 is configured to arrange the echo signals in the spatial relationship from which they were received in a desired image format. For instance, the scan converter 630 may arrange the echo signal into a two dimensional (2D) sector-shaped format, or a pyramidal or otherwise shaped three dimensional (3D) format. The multiplanar reformatter 632 can convert echoes which are received from points in a common plane in a volumetric region of the body into an ultrasonic image (e.g., a B-mode image) of that plane, for example as described in U.S. Pat. No. 6,443,896 (Detmer). A volume renderer 634 may generate an image of the 3D dataset as viewed from a given reference point, e.g., as described in U.S. Pat. No. 6,530,885 (Entrekin et al.).

The system 610 may also include a Doppler processor (not shown). The signals from the signal processor 626 may be coupled to the Doppler processor, which may be configured to estimate the Doppler shift and generate Doppler image data. The Doppler image data may include color data, which may be overlaid with B-mode (or grayscale) image data for display. The Doppler processor may be configured to estimate velocity and power in accordance with known techniques. For example, the Doppler processor may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators.

Output (e.g., images) from the scan converter 630, the multiplanar reformatter 632, and/or the volume renderer 634 may be coupled to an image processor 636 for further enhancement, buffering and temporary storage before being displayed on an image display 638. The display 638 may include a display device implemented using a variety of known display technologies, such as LCD, LED, OLED, or plasma display technology.

In accordance with the examples herein, the system 600 may include a processor 637, which is configured to perform functions associated with the automatic retrieval and reconfiguration of the acquisition parameters of system 600. For example, the processor 637 may implement (e.g., in a processor performing executable instructions) a neural network 642. The neural network 642 may include at least one multilayer network of artificial neural nodes trained to analyze pairs of ultrasound images to determine whether the images in the pair match. Any suitable types of algorithms (e.g., generative, discriminative, or combinations thereof) and/or architecture may be used for the neural network 642. In some examples, the neural network 642 may implement a deep neural network, such as a branched convolutional neural network configured to operate on the input images and connected to a top network for the ultimate determination of a match.

In any of the embodiments herein, some or all of the functions of multiple ones or all of the processors described may be combined into an integrated processing circuitry (the operations of which may be divided among multiple processor operating in parallel) rather than the specific functions described with reference to each of these components being performed by a discrete processing unit. For example, although described as separate processors, it will be understood that the functionality of any of the processors described herein (e.g., processors 640, 642, 636, etc.) may be implemented in a single processor (e.g., a CPU or GPU implementing the functionality of processor 637) or fewer number of processors than described in this example. More broadly, some or all of the functions of any of the processing components herein (e.g., processors 626, 628, 630, 632, 634, 640, 636, etc.) may be combined into a single or fewer number of integrated processing circuitry rather than implemented in discrete processors associated only with the specific functions described with reference to each of these components.

Figure 9:
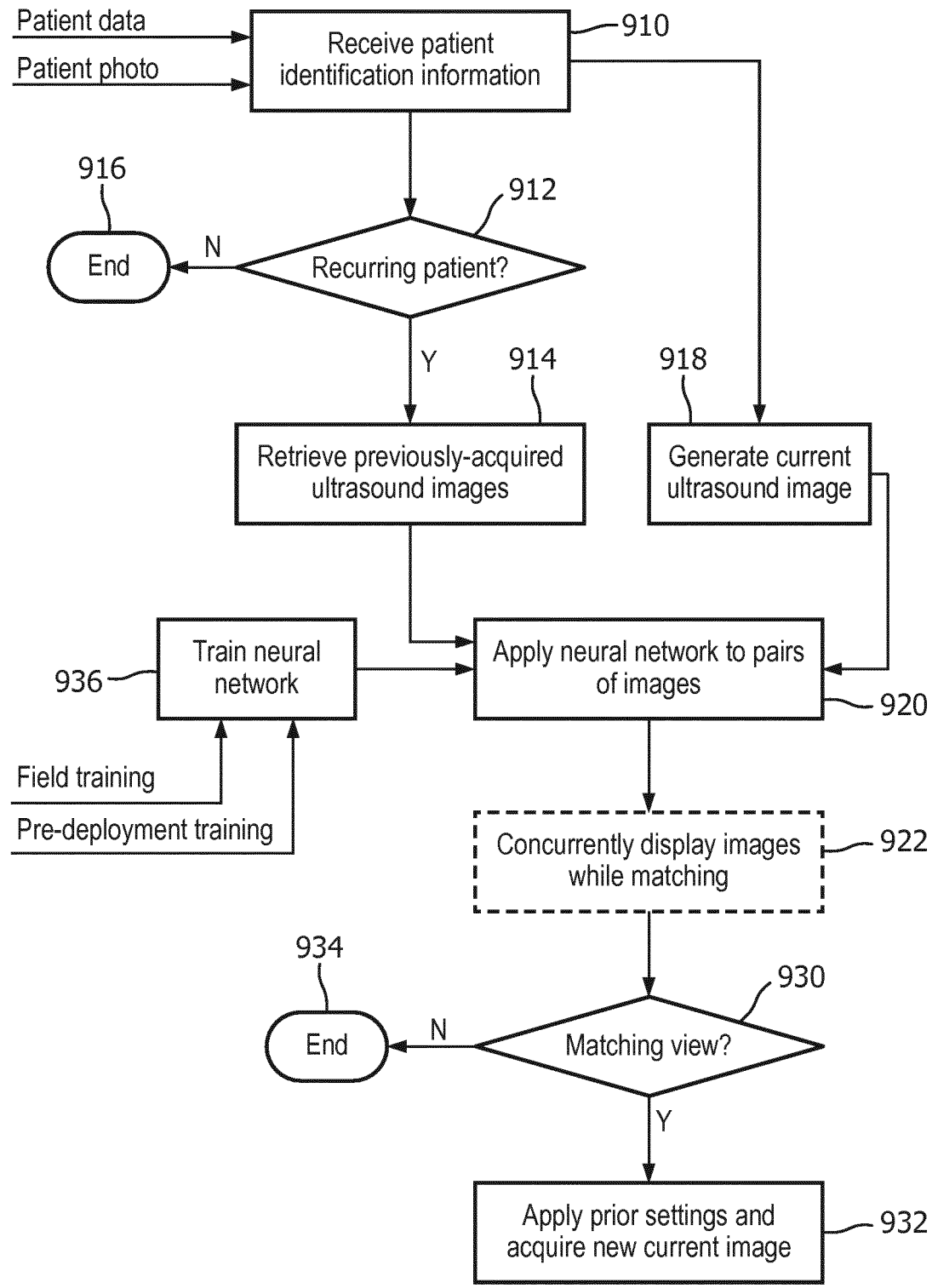
FIG. 9 shows a flow diagram of a process for ultrasound imaging in accordance with some examples herein.

FIG. 9 shows a flow diagram of an example method in accordance with embodiments of the present invention. The method 900 includes receiving patient identification information (block 910), determining whether the patient identification information identifies a recurring patient (block 912), and upon determination that the patient identification information identifies a recurring patient, automatically retrieving a plurality of previous ultrasound images associated with the recurring patient from a source of previously-acquired ultrasound image data (Block 914). If the system determines that the patient is not a recurring patient, the process terminates, at block 916.

The receiving of patient identification information may be performed in accordance with and include any of the examples herein. For example, patient identification information may be received responsive to user input (e.g., a user entering the patient's name, ID, date of birth, etc.) and may additionally include other identifying information such as patient photo. The determination of whether the patient identification information identifies a recurring patient may be may be performed in accordance with and include any of the examples herein. For example, the determination may be performed based by a rules-based algorithm, by a properly trained neural network, or a combination of the two, for example applying the algorithm to the text inputs (e.g., name, ID, etc.) and applying the neural network to the patient photo to perform face recognition.

As further shown in FIG. 9, the method 900 may further include generating a current ultrasound image of biological tissue of the recurring patient (block 918). The current ultrasound image may be generated in real time while ultrasonically scanning the patient. In some examples, the current ultrasound image may include a frame of a cineloop of image data presented to the user in real time. The current ultrasound image may be a 2D image or a 3D image. As shown further in block 920, the current ultrasound image and the plurality of previous ultrasound images may be provided to a neural network for the identification of a matching previous image. Upon the identification of a matching previous image at block 930, the method continues to block 932 to automatically adjust one or more imaging parameters of the ultrasound imaging system to correspond to imaging parameter settings associated with the matching previous image and acquire a new ultrasound image with the adjusted imaging parameters. The determination of a previous matching image may be made, for example, upon an identification of a previously acquired image of the recurring patient that represents the biological tissue at the same imaging plane as the imaging plane of the currently acquired ultrasound image. In contrast, if no match is found among the previous ultrasound data at block 930, the process of automatically configuring the system may terminate at block 934. In some embodiments, the method may further involve the concurrent display of the two images being matched (e.g., the current ultrasound image and a dynamically updating display that cycles through each of the previously acquired images as the comparison of the previous image with the current image is being performed) as shown in block 922.

In yet further examples, the method 900 may include training the neural network, as shown in block 936. Training of the neural network may involve preparing and presenting to a network in training, pre-deployment training dataset. Such training datasets may include multiple known pairs of images of the same target but at different views (e.g., at different imaging plane through a given tissue). In some cases, the training datasets may also include the imagining settings corresponding to each of the images in the pairs. The training inputs are labeled as either matching or non-matching (or labeled with one of a plurality of classifications if training the network to classify images in more than two classifications). The training data during the pre-deployment training may typically be split into a training set and a validation set. During the pre-deployment training, batches of training pairs from the training set are randomly selected and provided as inputs to the network. The validation set is used to validate the performance of the network at intermediate intervals and/or at the completion of training prior to deployment of the network. The pairs of images in the training set and the validation set may be distinct—that is, there is no exact same pair of images in the two sets. The weights of the network may be updated for example, using gradient descent with backpropagation. The training prior to deployment (i.e. to operate on unknown image pairs) may involve many epochs of parameter updating, and the pre-deployment training is deemed complete (see e.g., block 309 in FIG. 4) when the loss error on the validation set falls below a certain value. In some embodiments, the neural network may be further trained in the field with previously unknown data sets. For example, an imaging system may be configured to receive user input (e.g., confirmatory input of a match and/or additional input for adjusting imagining parameters after automatic parameters have been applied) and the results of such live imaging may then be used for subsequent (in the field or post-deployment) training of the neural network.

Although examples of producing medical images from sparsely sampled data are described herein with reference to ultrasound image data, it will be understood that the examples herein are equally applicable to training a neural network to produce images from a sparse dataset of any imaging modality, such as magnetic resonance imaging (MRI), computed tomography (CT), positron emission tomography (PET), and virtually any other imaging modality.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. An ultrasound imaging system for ultrasonically inspecting biological tissue of a patient, the system comprising:
    an ultrasound probe; and
    a processor communicatively coupled to the ultrasound probe and to a source of previously-acquired ultrasound image data, wherein the processor is configured to:
    provide a current ultrasound image of the biological tissue of the patient using current imaging parameter settings;
    retrieve, from the source of previously-acquired ultrasound image data, previous ultrasound images associated with the patient and previous imaging parameter settings associated with the previous ultrasound images;
    provide the current ultrasound image and the previous ultrasound images to at least one neural network, wherein the at least one neural network is trained to determine whether the current ultrasound image and the previous ultrasound images correspond to a same imaging plane through the biological tissue of the patient by performing operations comprising:
    receive, by the at least one neural network, the current ultrasound image in parallel with the current imaging parameter settings provided as a settings vector comprising values of ultrasound imaging parameter settings;
    convert the current ultrasound image, together with the settings vector, to a first feature vector,
    convert at least some of the previous ultrasound images, together with respective previous imaging parameter settings of the previous imaging parameter settings, to respective second feature vectors,
    compute respective distance metrics between the first feature vector and the respective second feature vectors, and
    determine a similarity between the current ultrasound image and the at least some of the previous ultrasound images using the computed respective distance metrics;
    cause a user interface to concurrently display the current ultrasound image and successive ones of the at least some of the previous ultrasound images as successive image pairs, wherein each of the successive ones of the at least some of the previous ultrasound images is displayed while determining whether the current ultrasound image and each successive one of the at least some of the previous ultrasound images correspond to the same imaging plane, and wherein the user interface dynamically updates to cycle through the successive image pairs;
    identify, via the at least one neural network, a previous ultrasound image of the previous ultrasound images that corresponds to the same imaging plane as the current ultrasound image, wherein the identified previous ultrasound image is included in the at least some of the previous ultrasound images;
    adjust one or more imaging parameters of the ultrasound imaging system to correspond to particular imaging parameter settings of the previous imaging parameter settings associated with the identified previous ultrasound image; and
    produce an updated ultrasound image with the adjusted imaging parameters, wherein the updated ultrasound image is different from the current ultrasound image and the previous ultrasound images.

2. The ultrasound imaging system of claim 1, wherein the processor is further configured to identify whether the patient is a recurring patient.

3. The ultrasound imaging system of claim 1, wherein the at least one neural network is trained to compare the first feature vector and the respective second feature vectors to produce a similarity score between the current ultrasound image and the at least some of the previous ultrasound images.

4. The ultrasound imaging system of claim 1, wherein the at least one neural network includes a plurality of neural network branches configured to operate in parallel.

5. The ultrasound imaging system of claim 1, wherein the at least one neural network includes a first portion comprising one or more neural networks configured to output the first feature vector and the respective second feature vectors, and a second portion configured to determine the similarity between the current ultrasound image and the at least some of the previous ultrasound images.

6. The ultrasound imaging system of claim 1, wherein the processor is further configured to cause the user interface to display a similarity score with each successive image pair.

7. The ultrasound imaging system of claim 1, wherein the processor is configured to determine the similarity between the current ultrasound image and the at least some of the previous ultrasound images irrespective of differences in pixel data between the current ultrasound image and the at least some of the previous ultrasound images.

8. The ultrasound imaging system of claim 1, wherein the distance metric includes a squared difference, a correlation analysis, or a combination thereof.

9. The ultrasound imaging system of claim 1, wherein the at least one neural network is configured to generate at least one feature map based on the current ultrasound image, the at least one feature map having a first dimension and a second dimension, wherein the settings vector is spatially tiled based on the first dimension or the second dimension, and wherein the spatially tiled settings vector is summed with the at least one feature map for further processing by the at least one neural network.

10. The ultrasound imaging system of claim 2, wherein the processor is configured to identify the patient as the recurring patient based on patient identification information received by the processor.

11. The ultrasound imaging system of claim 10, wherein the patient identification information includes an image received from a storage device or an image capture device different from the ultrasound probe, the image comprising a facial feature of the patient and wherein the processor is further configured to determine whether the patient identification information identifies the recurring patient based, in part, on the facial feature.

12. The ultrasound imaging system of claim 4, wherein a first branch of the plurality of neural network branches is configured to receive a first input comprising the current ultrasound image and a second branch of the plurality of neural network branches is configured to receive a second input comprising the at least some of the previous ultrasound images.

13. The ultrasound imaging system of claim 12, wherein the first branch of the plurality of neural network branches is further configured to receive a third input comprising the current imaging parameter settings and the second branch of the plurality of neural network branches is configured to receive a fourth input comprising the previous imaging parameter settings.

14. The ultrasound imaging system of claim 13, wherein each of the plurality of neural network branches comprises a convolutional neural network, and wherein the first branch is configured to output the first feature vector and the second branch is configured to output the respective second feature vectors.

15. The ultrasound imaging system of claim 5, wherein the second portion is configured to compute the respective distance metrics between the first feature vector and the respective second feature vectors.

16. The ultrasound imaging system of claim 15, wherein the second portion comprises at least one additional neural network trained to classify the first feature vector and the respective second feature vectors into one of a plurality of similarity categories.

17. A method of ultrasound imaging comprising:
receiving an indication of a recurring patient by at least one processor of an ultrasound imaging system;
responsive to the indication of the recurring patient, automatically retrieving a plurality of previous ultrasound images associated with the recurring patient and previous imaging parameter settings associated with the plurality of previous ultrasound images from a source of previously-acquired ultrasound image data;
generating a current ultrasound image of biological tissue of the recurring patient using current imaging parameter settings;
providing the current ultrasound image and the plurality of previous ultrasound images to a neural network to identify a matching previous image of the recurring patient, wherein the neural network identifies the matching previous image by:
receiving, by the at least one neural network, the current ultrasound imaging in parallel with the current imaging parameter settings provided as a settings vector comprising values of ultrasound imaging parameter settings;
converting the current ultrasound image, together with the settings vector to a first feature vector,
converting a previous ultrasound image of the plurality of previous ultrasound images, together with respective previous imaging parameter settings of the previous imaging parameter settings, to a second feature vector,
computing a distance metric between the first feature vector and the second feature vector, and
identifying the previous ultrasound image as the matching previous image based on the distance metric; and
causing a user interface to concurrently display the current ultrasound image and successive ones of the plurality of previous ultrasound images as successive image pairs, wherein each of the successive ones of the plurality of previous ultrasound images is displayed while determining whether the current ultrasound image and each successive one of the plurality of previous ultrasound images correspond to a same imaging plane, wherein determining whether the current ultrasound image and each successive one of the plurality of previous ultrasound images correspond to the same imaging plane includes identifying the matching previous image of the recurring patient, and wherein the user interface dynamically updates to cycle through the successive image pairs;
responsive to an identification of the matching previous image, automatically adjusting one or more imaging parameters of the ultrasound imaging system to correspond to particular imaging parameter settings of the previous imaging parameter settings associated with the matching previous image and acquiring a new ultrasound image with the adjusted imaging parameters.

18. The method of claim 17, further comprising:
receiving patient identification information by the at least one processor;
determining whether the patient is the recurring patient based on the patient identification information; and
generating the indication of the recurring patient responsive to a determination that the patient identification information identifies the recurring patient.

19. The method of claim 17, wherein the neural network includes a pair of neural networks operating in parallel, and wherein the providing the current ultrasound image and the plurality the previous ultrasound images to the neural network includes providing the current ultrasound image to a first neural network of the pair of neural networks and providing the previous ultrasound image to a second neural network of the pair of neural networks.

20. The method of claim 17, further comprising concurrently displaying a similarity score with each successive image pair of the successive image pairs.

21. The method of claim 18, wherein the patient identification information comprises an image received from a storage device or an image capture device, the image comprising a facial feature of the patient.

22. A non-transitory computer-readable medium comprising executable instructions that, when executed, cause a processor of a medical imaging system to perform the method of claim 17.

* * * * *